United States Patent
Levin

(10) Patent No.: US 8,135,876 B2
(45) Date of Patent: Mar. 13, 2012

(54) IDENTIFYING WHEN A USB SELF-POWERED DEVICE IS CONNECTED TO A MEDICAL DEVICE BY TRIGGERING AN ALERT ABOUT A POTENTIAL RISK TO PATIENT

(75) Inventor: Roland Levin, San Ramon, CA (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 155 days.

(21) Appl. No.: 12/347,297

(22) Filed: Dec. 31, 2008

(65) Prior Publication Data

US 2010/0169513 A1     Jul. 1, 2010

(51) Int. Cl.
*G06F 3/00* (2006.01)
*H02J 7/00* (2006.01)

(52) U.S. Cl. ............... 710/15; 710/14; 710/16; 710/18; 710/62; 710/305; 713/300; 713/310; 713/320; 713/322; 713/324; 713/340; 604/29; 604/27; 320/136; 320/114; 320/112

(58) Field of Classification Search ............. 710/62–64, 710/305, 14–19; 713/300, 310, 320, 322, 713/324, 340
See application file for complete search history.

(56) References Cited

U.S. PATENT DOCUMENTS

| | | | |
|---|---|---|---|
| 3,742,947 A * | 7/1973 | Hashem .................. | 600/508 |
| 3,886,932 A | 6/1975 | Suessmilch | |
| 4,976,681 A * | 12/1990 | Magro .................. | 600/17 |
| 5,324,422 A | 6/1994 | Colleran et al. | |
| 5,421,823 A | 6/1995 | Kamen et al. | |
| 5,431,626 A | 7/1995 | Bryant et al. | |
| 5,438,510 A | 8/1995 | Bryant et al. | |
| 5,575,807 A * | 11/1996 | Faller .................. | 607/5 |
| 5,615,091 A * | 3/1997 | Palatnik .................. | 363/17 |
| 5,903,211 A * | 5/1999 | Flego et al. ............ | 340/286.07 |
| 5,935,099 A | 8/1999 | Peterson et al. | |
| 6,503,062 B1 | 1/2003 | Gray et al. | |
| 6,665,806 B1 * | 12/2003 | Shimizu .................. | 713/324 |
| 6,808,369 B2 | 10/2004 | Gray et al. | |
| 6,814,547 B2 | 11/2004 | Childers et al. | |
| 6,929,751 B2 | 8/2005 | Bowman, Jr. et al. | |
| 7,083,719 B2 | 8/2006 | Bowman, Jr. et al. | |
| 7,124,307 B2 | 10/2006 | Sugita et al. | |
| 7,571,336 B2 * | 8/2009 | Barthe et al. .................. | 713/340 |
| 7,966,064 B2 * | 6/2011 | Hopermann et al. ............ | 607/2 |
| 8,030,891 B2 * | 10/2011 | Welsch et al. .................. | 320/114 |
| 2003/0172318 A1 | 9/2003 | Sugita et al. | |
| 2004/0113498 A1 * | 6/2004 | Kroenke .................. | 307/115 |
| 2004/0143297 A1 * | 7/2004 | Ramsey, III .................. | 607/5 |
| 2005/0001179 A1 * | 1/2005 | Gisler et al. .................. | 250/551 |
| 2006/0265540 A1 * | 11/2006 | Mass et al. .................. | 710/305 |

(Continued)

FOREIGN PATENT DOCUMENTS

EP       0 717 341 A1    6/1996

(Continued)

OTHER PUBLICATIONS

International Search Report for International Application No. PCT/US2009/067454 dated Apr. 8, 2010.

(Continued)

*Primary Examiner* — Tammara Peyton
(74) *Attorney, Agent, or Firm* — Fish & Richardson P.C.

(57) ABSTRACT

This patent application relates generally to identifying a self-powered device connected to a medical device.

57 Claims, 11 Drawing Sheets

U.S. PATENT DOCUMENTS

| | | | |
|---|---|---|---|
| 2007/0260783 A1 | 11/2007 | Combs et al. | |
| 2009/0177046 A1* | 7/2009 | Zhang et al. | 600/300 |
| 2009/0256527 A1* | 10/2009 | Welsch et al. | 320/136 |
| 2010/0026499 A1* | 2/2010 | Lamb | 340/573.1 |

FOREIGN PATENT DOCUMENTS

| | | |
|---|---|---|
| EP | 1 553 480 A1 | 7/2005 |
| JP | 2006-266951 | 10/2006 |
| WO | 2006/116480 | 11/2006 |

OTHER PUBLICATIONS

Universal Serial Bus Specification Revision 2.0, pp. 1-2; 239-296 (Apr. 27, 2000).

Product Data Sheet. Phillips ISP1521 Hi-Speed Universal Serial Bus hub controller. Rev. 04—Mar. 30, 2006.

Product Data Sheet. Burr-Brown Products from Texas Instruments. High-Side Measurement, Current Shunt Monitor. Dec. 1999, Revised Nov. 2005.

* cited by examiner

IDENTIFYING WHEN A USB SELF-POWERED DEVICE IS CONNECTED TO A MEDICAL DEVICE BY TRIGGERING AN ALERT ABOUT A POTENTIAL RISK TO PATIENT

TECHNICAL FIELD

This patent application relates generally to identifying a self-powered device connected to a medical device.

BACKGROUND

Medical devices traditionally have been designed to have an extremely low leakage current in order to prevent or limit safety risks to patients.

SUMMARY

In general, in some aspects, a method includes determining whether a universal serial bus (USB) peripheral device is connected to a medical device. The medical device is configured for use in a medical procedure with a patient. The method also includes, if the USB peripheral device is determined to be connected to the medical device, determining whether the USB peripheral device is drawing power from the medical device.

Implementations may include one or more of the following features.

The method may also include, if the USB peripheral device is determined to not be drawing power from the medical device, providing an indication of a potentially unsafe condition. The potentially unsafe condition may be that the USB peripheral device may be drawing power from a power supply independent of the medical device and thus may present a potential risk to the patient. Providing the indication may include at least one of the following: displaying a warning message on a user interface, or triggering an alarm. The medical device may include the user interface.

The method may also include, if the USB peripheral device is determined to not be drawing power from the medical device, electrically isolating the USB peripheral device from the medical device and the patient. Electrically isolating the USB peripheral device from the medical device and the patient may include disconnecting one or more signal lines connected to a USB port of the medical device. The USB port may be configured to receive a USB connector of the USB peripheral device. The one or more signal lines may include a first USB data line, a second USB data line, a USB power line, and a USB ground line.

In the method, the medical device may include a USB host device capable of providing power to the USB peripheral device. The USB peripheral device may include a USB connector. The USB host device may include a USB port to receive the USB connector so that the USB peripheral device can be connected to the medical device.

In the method, the medical device may include one or more processing devices. In the method, determining whether the USB peripheral device is connected to the medical device may include monitoring a first USB data line and a second USB data line using the one or more processing devices. In the method, determining whether the USB peripheral device is connected to the medical device may also include, if at least one of the first USB data line or the second USB data line goes to a high state, determining that the USB peripheral device is connected to the medical device.

In the method, the medical device may include one or more processing devices. In the method, determining whether the USB peripheral device is connected to the medical device may include triggering an interrupt of the one or more processing devices if at least one of a first USB data line or a second USB data line goes to a high state. In the method, determining whether the USB peripheral device is connected to the medical device may also include polling the first USB data line and the second USB data line using the one or more processing devices to confirm that the USB peripheral device is connected to the medical device.

In the method, the medical device may include one or more processing devices. In the method, determining whether the USB peripheral device is drawing power from the medical device may include monitoring an output of a current detection circuit using the one or more processing devices. The medical device may include the current detection circuit. In the method, determining whether the USB peripheral device is drawing power from the medical device may also include, if the output is at a low state, determining that the USB peripheral device is not drawing power from the medical device. In the method, the current detection circuit may include an operational amplifier, a first resistor, a second resistor, and a third resistor. The operational amplifier may include a positive input, a negative input, and the output of the current detection circuit. The first resistor may be connected between a power supply of the medical device and the positive input. The second resistor may be connected between a signal ground of the medical device and the positive input. The first and the second resistors may form a voltage divider between the power supply and the signal ground. The third resistor may be connected between the power supply and the negative input. In the method, the output may be at a low state when a first voltage at the positive input is less than a second voltage at the negative input.

In the method, the medical procedure may include hemodialysis and the medical device may include a hemodialysis device.

In the method, the medical procedure may include an extracorporeal medical procedure in which a portion of blood may be removed from the patient, the portion of the blood may be processed by the medical device, and at least some of the portion of blood may be subsequently returned to the patient.

In the method, the medical procedure may include at least one of hemodialysis, peritoneal dialysis, hemofiltration, hemodiafiltration, plasmapheresis, apheresis, extracorporeal membrane oxygenation, or cardiopulmonary bypass.

In the method, the medical procedure may include peritoneal dialysis and the medical device may include a peritoneal dialysis device.

In the method, the medical procedure may include infusing medication into the patient's body and the medical device may include an infusion pump.

In the method, the medical procedure may include entering the patient's body and the medical device may include a surgical instrument.

In the method, the medical procedure may include a medical procedure involving at least one of direct contact of the medical device with a bodily fluid of the patient, direct contact of an output of the medical device with the patient, direct contact of the medical device with the patient's body, or puncturing of the patient's skin.

In some aspects, a medical device includes a memory and one or more processing devices. The memory is configured to store instructions for execution. The one or more processing devices are configured to execute the instructions. The instructions are for causing the one or more processing devices to determine whether a universal serial bus (USB) peripheral device is connected to the medical device. The medical device is configured for use in a medical procedure with a patient. The instructions are also for causing the one or more processing devices to, if the USB peripheral device is determined to be connected to the medical device, determine whether the USB peripheral device is drawing power from the medical device.

Implementations may include one or more of the following features.

In the medical device, the instructions may also include instructions for causing the one or more processing devices to, if the USB peripheral device is determined to not be drawing power from the medical device, provide an indication of a potentially unsafe condition. The potentially unsafe condition may be that the USB peripheral device may be drawing power from a power supply independent of the medical device and thus may present a potential risk to the patient. Providing the indication may include at least one of the following: displaying a warning message on a user interface, or triggering an alarm. The medical device may include the user interface.

In the medical device, the instructions may also include instructions for causing the one or more processing devices to, if the USB peripheral device is determined to not be drawing power from the medical device, electrically isolate the USB peripheral device from the medical device and the patient. Electrically isolating the USB peripheral device from the medical device and the patient may include disconnecting one or more signal lines connected to a USB port of the medical device. The USB port may be configured to receive a USB connector of the USB peripheral device. The one or more signal lines may include a first USB data line, a second USB data line, a USB power line, and a USB ground line.

The medical device may include a USB host device capable of providing power to the USB peripheral device. The USB peripheral device may include a USB connector. The USB host device may include a USB port to receive the USB connector so that the USB peripheral device can be connected to the medical device. The USB host device may include the memory and the one or more processing devices.

In the medical device, determining whether the USB peripheral device is connected to the medical device may include monitoring a first USB data line and a second USB data line. In the medical device, determining whether the USB peripheral device is connected to the medical device may also include, if at least one of the first USB data line or the second USB data line goes to a high state, determining that the USB peripheral device is connected to the medical device.

In the medical device, determining whether the USB peripheral device is connected to the medical device may include triggering an interrupt of the one or more processing devices if at least one of a first USB data line or a second USB data line goes to a high state. In the medical device, determining whether the USB peripheral device is connected to the medical device may also include polling the first USB data line and the second USB data line to confirm that the USB peripheral device is connected to the medical device.

The medical device may also include a current detection circuit. In the medical device, determining whether the USB peripheral device is drawing power from the medical device may include monitoring an output of the current detection circuit. In the medical device, determining whether the USB peripheral device is drawing power from the medical device may also include, if the output is at a low state, determining that the USB peripheral device is not drawing power from the medical device. In the medical device, the current detection circuit may include an operational amplifier, a first resistor, a second resistor, and a third resistor. The operational amplifier may include a positive input, a negative input, and the output of the current detection circuit. The first resistor may be connected between a power supply of the medical device and the positive input. The second resistor may be connected between a signal ground of the medical device and the positive input. The first and the second resistors may form a voltage divider between the power supply and the signal ground. The third resistor may be connected between the power supply and the negative input. In the medical device, the output may be at a low state when a first voltage at the positive input is less than a second voltage at the negative input.

In the medical device, the medical procedure may include hemodialysis and the medical device may include a hemodialysis device.

In the medical device, the medical procedure may include an extracorporeal medical procedure in which a portion of blood may be removed from the patient, the portion of the blood may be processed by the medical device, and at least some of the portion of blood may be subsequently returned to the patient.

In the medical device, the medical procedure may include at least one of hemodialysis, peritoneal dialysis, hemofiltration, hemodiafiltration, plasmapheresis, apheresis, extracorporeal membrane oxygenation, or cardiopulmonary bypass.

In the medical device, the medical procedure may include peritoneal dialysis and the medical device may include a peritoneal dialysis device.

In the medical device, the medical procedure may include infusing medication into the patient's body and the medical device may include an infusion pump.

In the medical device, the medical procedure may include entering the patient's body and the medical device may include a surgical instrument.

In the medical device, the medical procedure may include a medical procedure involving at least one of direct contact of the medical device with a bodily fluid of the patient, direct contact of an output of the medical device with the patient, direct contact of the medical device with the patient's body, or puncturing of the patient's skin.

In some aspects, one or more computer-readable media store executable instructions. The one or more computer-readable media include tangible media. The instructions are for causing one or more processing devices to determine whether a universal serial bus (USB) peripheral device is connected to a medical device. The medical device includes the one or more processing devices. The medical device is configured for use in a medical procedure with a patient. The instructions are also for causing the one or more processing devices to, if the USB peripheral device is determined to be connected to the medical device, determine whether the USB peripheral device is drawing power from the medical device.

Implementations may include one or more of the following features.

In the one or more computer-readable media, the instructions may also include instructions for causing the one or more processing devices to, if the USB peripheral device is determined to not be drawing power from the medical device, provide an indication of a potentially unsafe condition. The potentially unsafe condition may be that the USB peripheral device may be drawing power from a power supply independent of the medical device and thus may present a potential risk to the patient. Providing the indication may include at least one of the following: displaying a warning message on a user interface, or triggering an alarm. The medical device may include the user interface.

In the one or more computer-readable media, the instructions may also include instructions for causing the one or more processing devices to, if the USB peripheral device is determined to not be drawing power from the medical device, electrically isolate the USB peripheral device from the medical device and the patient. Electrically isolating the USB peripheral device from the medical device and the patient may include disconnecting one or more signal lines connected to a USB port of the medical device. The USB port may be configured to receive a USB connector of the USB peripheral device. The one or more signal lines may include a first USB data line, a second USB data line, a USB power line, and a USB ground line.

In the one or more computer-readable media, the medical device may include a USB host device capable of providing power to the USB peripheral device. The USB peripheral device may include a USB connector. The USB host device may include a USB port to receive the USB connector so that the USB peripheral device can be connected to the medical device.

In the one or more computer-readable media, determining whether the USB peripheral device is connected to the medical device may include monitoring a first USB data line and a second USB data line. In the one or more computer-readable media, determining whether the USB peripheral device is connected to the medical device may also include, if at least one of the first USB data line or the second USB data line goes to a high state, determining that the USB peripheral device is connected to the medical device.

In the one or more computer-readable media, determining whether the USB peripheral device is connected to the medical device may include triggering an interrupt of the one or more processing devices if at least one of a first USB data line or a second USB data line goes to a high state. In the one or more computer-readable media, determining whether the USB peripheral device is connected to the medical device may also include polling the first USB data line and the second USB data line to confirm that the USB peripheral device is connected to the medical device.

In the one or more computer-readable media, determining whether the USB peripheral device is drawing power from the medical device may include monitoring an output of a current detection circuit. The medical device may include the current detection circuit. In the one or more computer-readable media, determining whether the USB peripheral device is drawing power from the medical device may also include, if the output is at a low state, determining that the USB peripheral device is not drawing power from the medical device. In the one or more computer-readable media, the current detection circuit may include an operational amplifier, a first resistor, a second resistor, and a third resistor. The operational amplifier may include a positive input, a negative input, and the output of the current detection circuit. The first resistor may be connected between a power supply of the medical device and the positive input. The second resistor may be connected between a signal ground of the medical device and the positive input. The first and the second resistors may form a voltage divider between the power supply and the signal ground. The third resistor may be connected between the power supply and the negative input. In the one or more computer-readable media, the output may be at a low state when a first voltage at the positive input is less than a second voltage at the negative input.

In the one or more computer-readable media, the medical procedure may include hemodialysis and the medical device may include a hemodialysis device.

In the one or more computer-readable media, the medical procedure may include an extracorporeal medical procedure in which a portion of blood may be removed from the patient, the portion of the blood may be processed by the medical device, and at least some of the portion of blood may be subsequently returned to the patient.

In the one or more computer-readable media, the medical procedure may include at least one of hemodialysis, peritoneal dialysis, hemofiltration, hemodiafiltration, plasmapheresis, apheresis, extracorporeal membrane oxygenation, or cardiopulmonary bypass.

In the one or more computer-readable media, the medical procedure may include peritoneal dialysis and the medical device may include a peritoneal dialysis device.

In the one or more computer-readable media, the medical procedure may include infusing medication into the patient's body and the medical device may include an infusion pump.

In the one or more computer-readable media, the medical procedure may include entering the patient's body and the medical device may include a surgical instrument.

In the one or more computer-readable media, the medical procedure may include a medical procedure involving at least one of direct contact of the medical device with a bodily fluid of the patient, direct contact of an output of the medical device with the patient, direct contact of the medical device with the patient's body, or puncturing of the patient's skin.

In general, in some aspects, a method includes determining that a universal serial bus (USB) peripheral device is not drawing power from a medical device. The USB peripheral device is connected to the medical device. The medical device is configured for use in a medical procedure with a patient. The method also includes, responsively to the determining, providing an indication of a potentially unsafe condition to at least one of a user of the medical device or the patient. The potentially unsafe condition is that the USB peripheral device may be drawing power from a power supply independent of the medical device and thus may present a potential risk to the patient.

Implementations may include one or more of the following features.

In the method, the medical procedure may include hemodialysis and the medical device may include a hemodialysis device.

In some aspects, a medical device includes a memory and one or more processing devices. The memory is configured to store instructions for execution. The one or more processing devices are configured to execute the instructions. The instructions are for causing the one or more processing devices to determine that a universal serial bus (USB) peripheral device connected to the medical device is not drawing power from the medical device. The medical device is configured for use in a medical procedure with a patient. The instructions are also for causing the one or more processing devices to, responsively to the determining, provide an indication of a potentially unsafe condition to at least one of a user of the medical device or the patient. The potentially unsafe condition is that the USB peripheral device may be drawing power from a power supply independent of the medical device and thus may present a potential risk to the patient.

Implementations may include one or more of the following features.

In the medical device, the medical procedure may include hemodialysis and the medical device may include a hemodialysis device.

In some aspects, one or more computer-readable media store executable instructions. The one or more computer-readable media include tangible media. The instructions are for causing one or more processing devices to determine that a universal serial bus (USB) peripheral device connected to a medical device is not drawing power from the medical device. The medical device includes the one or more processing devices. The medical device is configured for use in a medical procedure with a patient. The instructions are also for causing the one or more processing devices to, responsively to the determining, provide an indication of a potentially unsafe condition to at least one of a user of the medical device or the patient. The potentially unsafe condition is that the USB peripheral device may be drawing power from a power supply independent of the medical device and thus may present a potential risk to the patient.

Implementations may include one or more of the following features.

In the one or more computer-readable media, the medical procedure may include hemodialysis and the medical device may include a hemodialysis device.

In general, in some aspects, a method includes monitoring a first universal serial bus (USB) data line and a second USB data line on a medical device. The medical device is configured for use in a medical procedure with a patient. The method also includes, if at least one of the first USB data line or the second USB data line goes to a high state, monitoring an output of a current detection circuit. The output is indicative of whether power is or is not being drawn from the medical device by a USB peripheral device connected to the medical device.

Implementations may include one or more of the following features.

The method may also include, if the output indicates that power is not being drawn from the medical device by the USB peripheral device, performing at least one of the following: electrically isolating the USB peripheral device from the medical device and the patient; or providing an indication of a potentially unsafe condition. The potentially unsafe condition may be that the USB peripheral device may be drawing power from a power supply independent of the medical device and thus may present a potential risk to the patient.

In the method, the medical device may include one or more processing devices. In the method, monitoring the first USB data line and the second USB data line, and monitoring the output of the current detection may include monitoring the first USB data line and the second USB data line using the one or more processing devices; and monitoring the output of the current detection circuit using the one or more processing devices. In the method, the medical device may include a USB host device capable of providing power to the USB peripheral device. The USB peripheral device may include a USB connector. The USB host device may include a USB port to receive the USB connector so that the USB peripheral device can be connected to the medical device.

In the method, the medical procedure may include hemodialysis and the medical device may include a hemodialysis device.

In some aspects, a medical device includes a current detection circuit, a memory, and one or more processing devices. The memory is configured to store instructions for execution. The one or more processing devices are configured to execute the instructions. The instructions are for causing the one or more processing devices to monitor a first universal serial bus (USB) data line and a second USB data line on the medical device. The medical device is configured for use in a medical procedure with a patient. The instructions are also for causing the one or more processing devices to, if at least one of the first USB data line or the second USB data line goes to a high state, monitor an output of the current detection circuit. The output is indicative of whether power is or is not being drawn from the medical device by a USB peripheral device connected to the medical device.

Implementations may include one or more of the following features.

In the medical device, the instructions may also include instructions for causing the one or more processing devices to, if the output indicates that power is not being drawn from the medical device by the USB peripheral device, perform at least one of the following: electrically isolating the USB peripheral device from the medical device and the patient; or providing an indication of a potentially unsafe condition. The potentially unsafe condition may be that the USB peripheral device may be drawing power from a power supply independent of the medical device and thus may present a potential risk to the patient.

The medical device may include a USB host device capable of providing power to the USB peripheral device. The USB peripheral device may include a USB connector. The USB host device may include a USB port to receive the USB connector so that the USB peripheral device can be connected to the medical device. The USB host device may include the memory and the one or more processing devices In the medical device, the medical procedure may include hemodialysis and the medical device may include a hemodialysis device.

In some aspects, one or more computer-readable media store executable instructions. The one or more computer-readable media include tangible media. The instructions are for causing one or more processing devices to monitor a first universal serial bus (USB) data line and a second USB data line on a medical device. The medical device includes the one or more processing devices. The medical device is configured for use in a medical procedure with a patient. The instructions are also for causing the one or more processing devices to, if at least one of the first USB data line or the second USB data line goes to a high state, monitor an output of a current detection circuit. The output is indicative of whether power is or is not being drawn from the medical device by a USB peripheral device connected to the medical device.

Implementations may include one or more of the following features.

In the one or more computer-readable media, the instructions may also include instructions for causing the one or more processing devices to, if the output indicates that power is not being drawn from the medical device by the USB peripheral device, perform at least one of the following: electrically isolating the USB peripheral device from the medical device and the patient; or providing an indication of a potentially unsafe condition. The potentially unsafe condition may be that the USB peripheral device may be drawing power from a power supply independent of the medical device and thus may present a potential risk to the patient.

In the one or more computer-readable media, the medical device may include a USB host device capable of providing power to the USB peripheral device. The USB peripheral device may include a USB connector. The USB host device may include a USB port to receive the USB connector so that the USB peripheral device can be connected to the medical device.

In the one or more computer-readable media, the medical procedure may include hemodialysis and the medical device may include a hemodialysis device.

In some aspects, a method includes determining whether a universal serial bus (USB) peripheral device is connected to a dialysis device. The dialysis device is configured for use in a dialysis procedure with a patient. The method also includes, if the USB peripheral device is determined to be connected to the dialysis device, determining whether the USB peripheral device is drawing power from the dialysis device.

Implementations may include one or more of the following features.

The method may also include, if the USB peripheral device is determined to not be drawing power from the dialysis device, providing an indication of a potentially unsafe condition. The potentially unsafe condition may be that the USB peripheral device may be drawing power from a power supply independent of the dialysis device and thus may present a potential risk to the patient. Providing the indication may include at least one of the following: displaying a warning message on a user interface, or triggering an alarm. The dialysis device may include the user interface.

The method may also include, if the USB peripheral device is determined to not be drawing power from the dialysis device, electrically isolating the USB peripheral device from the dialysis device and the patient. Electrically isolating the USB peripheral device from the dialysis device and the patient may include disconnecting one or more signal lines connected to a USB port of the dialysis device. The USB port may be configured to receive a USB connector of the USB peripheral device. The one or more signal lines may include a first USB data line, a second USB data line, a USB power line, and a USB ground line.

In the method, the dialysis device may include a USB host device capable of providing power to the USB peripheral device. The USB peripheral device may include a USB connector. The USB host device may include a USB port to receive the USB connector so that the USB peripheral device can be connected to the dialysis device.

In the method, the dialysis device may include one or more processing devices. In the method, determining whether the USB peripheral device is connected to the dialysis device may include monitoring a first USB data line and a second USB data line using the one or more processing devices. In the method, determining whether the USB peripheral device is connected to the dialysis device may also include, if at least one of the first USB data line or the second USB data line goes to a high state, determining that the USB peripheral device is connected to the dialysis device.

In the method, the dialysis device may include one or more processing devices. In the method, determining whether the USB peripheral device is connected to the dialysis device may include triggering an interrupt of the one or more processing devices if at least one of a first USB data line or a second USB data line goes to a high state. In the method, determining whether the USB peripheral device is connected to the dialysis device may also include polling the first USB data line and the second USB data line using the one or more processing devices to confirm that the USB peripheral device is connected to the dialysis device.

In the method, the dialysis device may include one or more processing devices. In the method, determining whether the USB peripheral device is drawing power from the dialysis device may include monitoring an output of a current detection circuit using the one or more processing devices. The dialysis device may include the current detection circuit. In the method, determining whether the USB peripheral device is drawing power from the dialysis device may also include, if the output is at a low state, determining that the USB peripheral device is not drawing power from the dialysis device. In the method, the current detection circuit may include an operational amplifier, a first resistor, a second resistor, and a third resistor. The operational amplifier may include a positive input, a negative input, and the output of the current detection circuit. The first resistor may be connected between a power supply of the dialysis device and the positive input. The second resistor may be connected between a signal ground of the dialysis device and the positive input. The first and the second resistors may form a voltage divider between the power supply and the signal ground. The third resistor may be connected between the power supply and the negative input. In the method, the output may be at a low state when a first voltage at the positive input is less than a second voltage at the negative input.

In the method, the dialysis procedure may include hemodialysis and the dialysis device may include a hemodialysis device.

In the method, the dialysis procedure may include an extracorporeal dialysis procedure in which a portion of blood may be removed from the patient, the portion of the blood may be processed by the dialysis device, and at least some of the portion of blood may be subsequently returned to the patient.

In the method, the dialysis procedure may include peritoneal dialysis and the dialysis device may include a peritoneal dialysis device.

In some aspects, a dialysis device includes a memory and one or more processing devices. The memory is configured to store instructions for execution. The one or more processing devices are configured to execute the instructions. The instructions are for causing the one or more processing devices to determine whether a universal serial bus (USB) peripheral device is connected to the dialysis device. The dialysis device is configured for use in a dialysis procedure with a patient. The instructions are also for causing the one or more processing devices to, if the USB peripheral device is determined to be connected to the dialysis device, determine whether the USB peripheral device is drawing power from the dialysis device.

Implementations may include one or more of the following features.

In the dialysis device, the instructions may also include instructions for causing the one or more processing devices to, if the USB peripheral device is determined to not be drawing power from the dialysis device, provide an indication of a potentially unsafe condition. The potentially unsafe condition may be that the USB peripheral device may be drawing power from a power supply independent of the dialysis device and thus may present a potential risk to the patient. Providing the indication may include at least one of the following: displaying a warning message on a user interface, or triggering an alarm. The dialysis device may include the user interface.

In the dialysis device, the instructions may also include instructions for causing the one or more processing devices to, if the USB peripheral device is determined to not be drawing power from the dialysis device, electrically isolate the USB peripheral device from the dialysis device and the patient. Electrically isolating the USB peripheral device from the dialysis device and the patient may include disconnecting one or more signal lines connected to a USB port of the dialysis device. The USB port may be configured to receive a USB connector of the USB peripheral device. The one or more signal lines may include a first USB data line, a second USB data line, a USB power line, and a USB ground line.

The dialysis device may include a USB host device capable of providing power to the USB peripheral device. The USB peripheral device may include a USB connector. The USB host device may include a USB port to receive the USB connector so that the USB peripheral device can be connected to the dialysis device. The USB host device may include the memory and the one or more processing devices.

In the dialysis device, determining whether the USB peripheral device is connected to the dialysis device may include monitoring a first USB data line and a second USB data line. In the dialysis device, determining whether the USB peripheral device is connected to the dialysis device may also include, if at least one of the first USB data line or the second USB data line goes to a high state, determining that the USB peripheral device is connected to the dialysis device.

In the dialysis device, determining whether the USB peripheral device is connected to the dialysis device may include triggering an interrupt of the one or more processing devices if at least one of a first USB data line or a second USB data line goes to a high state. In the dialysis device, determining whether the USB peripheral device is connected to the dialysis device may also include polling the first USB data line and the second USB data line to confirm that the USB peripheral device is connected to the dialysis device.

The dialysis device may also include a current detection circuit. In the dialysis device, determining whether the USB peripheral device is drawing power from the dialysis device may include monitoring an output of the current detection circuit. In the dialysis device, determining whether the USB peripheral device is drawing power from the dialysis device may also include, if the output is at a low state, determining that the USB peripheral device is not drawing power from the dialysis device. In the dialysis device, the current detection circuit may include an operational amplifier, a first resistor, a second resistor, and a third resistor. The operational amplifier may include a positive input, a negative input, and the output of the current detection circuit. The first resistor may be connected between a power supply of the dialysis device and the positive input. The second resistor may be connected between a signal ground of the dialysis device and the positive input. The first and the second resistors may form a voltage divider between the power supply and the signal ground. The third resistor may be connected between the power supply and the negative input. In the dialysis device, the output may be at a low state when a first voltage at the positive input is less than a second voltage at the negative input.

In the dialysis device, the dialysis procedure may include hemodialysis and the dialysis device may include a hemodialysis device.

In the dialysis device, the dialysis procedure may include an extracorporeal dialysis procedure in which a portion of blood may be removed from the patient, the portion of the blood may be processed by the dialysis device, and at least some of the portion of blood may be subsequently returned to the patient.

In the dialysis device, the dialysis procedure may include peritoneal dialysis and the dialysis device may include a peritoneal dialysis device.

In some aspects, one or more computer-readable media store executable instructions. The one or more computer-readable media include tangible media. The instructions are for causing one or more processing devices to determine whether a universal serial bus (USB) peripheral device is connected to a dialysis device. The dialysis device includes the one or more processing devices. The dialysis device is configured for use in a dialysis procedure with a patient. The instructions are also for causing the one or more processing devices to, if the USB peripheral device is determined to be connected to the dialysis device, determine whether the USB peripheral device is drawing power from the dialysis device.

Implementations may include one or more of the following features.

In the one or more computer-readable media, the instructions may also include instructions for causing the one or more processing devices to, if the USB peripheral device is determined to not be drawing power from the dialysis device, provide an indication of a potentially unsafe condition. The potentially unsafe condition may be that the USB peripheral device may be drawing power from a power supply independent of the dialysis device and thus may present a potential risk to the patient. Providing the indication may include at least one of the following: displaying a warning message on a user interface, or triggering an alarm. The dialysis device may include the user interface.

In the one or more computer-readable media, the instructions may also include instructions for causing the one or more processing devices to, if the USB peripheral device is determined to not be drawing power from the dialysis device, electrically isolate the USB peripheral device from the dialysis device and the patient. Electrically isolating the USB peripheral device from the dialysis device and the patient may include disconnecting one or more signal lines connected to a USB port of the dialysis device. The USB port may be configured to receive a USB connector of the USB peripheral device. The one or more signal lines may include a first USB data line, a second USB data line, a USB power line, and a USB ground line.

In the one or more computer-readable media, the dialysis device may include a USB host device capable of providing power to the USB peripheral device. The USB peripheral device may include a USB connector. The USB host device may include a USB port to receive the USB connector so that the USB peripheral device can be connected to the dialysis device.

In the one or more computer-readable media, determining whether the USB peripheral device is connected to the dialysis device may include monitoring a first USB data line and a second USB data line. In the one or more computer-readable media, determining whether the USB peripheral device is connected to the dialysis device may also include, if at least one of the first USB data line or the second USB data line goes to a high state, determining that the USB peripheral device is connected to the dialysis device.

In the one or more computer-readable media, determining whether the USB peripheral device is connected to the dialysis device may include triggering an interrupt of the one or more processing devices if at least one of a first USB data line or a second USB data line goes to a high state. In the one or more computer-readable media, determining whether the USB peripheral device is connected to the dialysis device may also include polling the first USB data line and the second USB data line to confirm that the USB peripheral device is connected to the dialysis device.

In the one or more computer-readable media, determining whether the USB peripheral device is drawing power from the dialysis device may include monitoring an output of a current detection circuit. The dialysis device may include the current detection circuit. In the one or more computer-readable media, determining whether the USB peripheral device is drawing power from the dialysis device may also include, if the output is at a low state, determining that the USB peripheral device is not drawing power from the dialysis device. In the one or more computer-readable media, the current detection circuit may include an operational amplifier, a first resistor, a second resistor, and a third resistor. The operational amplifier may include a positive input, a negative input, and the output of the current detection circuit. The first resistor may be connected between a power supply of the dialysis device and the positive input. The second resistor may be connected between a signal ground of the dialysis device and the positive input. The first and the second resistors may form a voltage divider between the power supply and the signal ground. The third resistor may be connected between the power supply and the negative input. In the one or more computer-readable media, the output may be at a low state when a first voltage at the positive input is less than a second voltage at the negative input.

In the one or more computer-readable media, the dialysis procedure may include hemodialysis and the dialysis device may include a hemodialysis device.

In the one or more computer-readable media, the dialysis procedure may include an extracorporeal dialysis procedure in which a portion of blood may be removed from the patient, the portion of the blood may be processed by the dialysis device, and at least some of the portion of blood may be subsequently returned to the patient.

In the one or more computer-readable media, the dialysis procedure may include peritoneal dialysis and the dialysis device may include a peritoneal dialysis device.

In general, in some aspects, a method includes determining that a universal serial bus (USB) peripheral device is not drawing power from a dialysis device. The USB peripheral device is connected to the dialysis device. The dialysis device is configured for use in a dialysis procedure with a patient. The method also includes, responsively to the determining, providing an indication of a potentially unsafe condition to at least one of a user of the dialysis device or the patient. The potentially unsafe condition is that the USB peripheral device may be drawing power from a power supply independent of the dialysis device and thus may present a potential risk to the patient.

Implementations may include one or more of the following features.

In the method, the dialysis procedure may include hemodialysis and the dialysis device may include a hemodialysis device.

In some aspects, a dialysis device includes a memory and one or more processing devices. The memory is configured to store instructions for execution. The one or more processing devices are configured to execute the instructions. The instructions are for causing the one or more processing devices to determine that a universal serial bus (USB) peripheral device connected to the dialysis device is not drawing power from the dialysis device. The dialysis device is configured for use in a dialysis procedure with a patient. The instructions are also for causing the one or more processing devices to, responsively to the determining, provide an indication of a potentially unsafe condition to at least one of a user of the dialysis device or the patient. The potentially unsafe condition is that the USB peripheral device may be drawing power from a power supply independent of the dialysis device and thus may present a potential risk to the patient.

Implementations may include one or more of the following features.

In the dialysis device, the dialysis procedure may include hemodialysis and the dialysis device may include a hemodialysis device.

In some aspects, one or more computer-readable media store executable instructions. The one or more computer-readable media include tangible media. The instructions are for causing one or more processing devices to determine that a universal serial bus (USB) peripheral device connected to a dialysis device is not drawing power from the dialysis device. The dialysis device includes the one or more processing devices. The dialysis device is configured for use in a dialysis procedure with a patient. The instructions are also for causing the one or more processing devices to, responsively to the determining, provide an indication of a potentially unsafe condition to at least one of a user of the dialysis device or the patient. The potentially unsafe condition is that the USB peripheral device may be drawing power from a power supply independent of the dialysis device and thus may present a potential risk to the patient.

Implementations may include one or more of the following features.

In the one or more computer-readable media, the dialysis procedure may include hemodialysis and the dialysis device may include a hemodialysis device.

In general, in some aspects, a method includes monitoring a first universal serial bus (USB) data line and a second USB data line on a dialysis device. The dialysis device is configured for use in a dialysis procedure with a patient. The method also includes, if at least one of the first USB data line or the second USB data line goes to a high state, monitoring an output of a current detection circuit. The output is indicative of whether power is or is not being drawn from the dialysis device by a USB peripheral device connected to the dialysis device.

Implementations may include one or more of the following features.

The method may also include, if the output indicates that power is not being drawn from the dialysis device by the USB peripheral device, performing at least one of the following: electrically isolating the USB peripheral device from the dialysis device and the patient; or providing an indication of a potentially unsafe condition. The potentially unsafe condition may be that the USB peripheral device may be drawing power from a power supply independent of the dialysis device and thus may present a potential risk to the patient.

In the method, the dialysis device may include one or more processing devices. In the method, monitoring the first USB data line and the second USB data line, and monitoring the output of the current detection may include monitoring the first USB data line and the second USB data line using the one or more processing devices; and monitoring the output of the current detection circuit using the one or more processing devices. In the method, the dialysis device may include a USB host device capable of providing power to the USB peripheral device. The USB peripheral device may include a USB connector. The USB host device may include a USB port to receive the USB connector so that the USB peripheral device can be connected to the dialysis device.

In the method, the dialysis procedure may include hemodialysis and the dialysis device may include a hemodialysis device.

In some aspects, a dialysis device includes a current detection circuit, a memory, and one or more processing devices. The memory is configured to store instructions for execution. The one or more processing devices are configured to execute the instructions. The instructions are for causing the one or more processing devices to monitor a first universal serial bus (USB) data line and a second USB data line on the dialysis device. The dialysis device is configured for use in a dialysis procedure with a patient. The instructions are also for causing the one or more processing devices to, if at least one of the first USB data line or the second USB data line goes to a high state, monitor an output of the current detection circuit. The output is indicative of whether power is or is not being drawn from the dialysis device by a USB peripheral device connected to the dialysis device.

Implementations may include one or more of the following features.

In the dialysis device, the instructions may also include instructions for causing the one or more processing devices to, if the output indicates that power is not being drawn from the dialysis device by the USB peripheral device, perform at least one of the following: electrically isolating the USB peripheral device from the dialysis device and the patient; or providing an indication of a potentially unsafe condition. The potentially unsafe condition may be that the USB peripheral device may be drawing power from a power supply independent of the dialysis device and thus may present a potential risk to the patient.

The dialysis device may include a USB host device capable of providing power to the USB peripheral device. The USB peripheral device may include a USB connector. The USB host device may include a USB port to receive the USB connector so that the USB peripheral device can be connected to the dialysis device. The USB host device may include the memory and the one or more processing devices In the dialysis device, the dialysis procedure may include hemodialysis and the dialysis device may include a hemodialysis device.

In some aspects, one or more computer-readable media store executable instructions. The one or more computer-readable media include tangible media. The instructions are for causing one or more processing devices to monitor a first universal serial bus (USB) data line and a second USB data line on a dialysis device. The dialysis device includes the one or more processing devices. The dialysis device is configured for use in a dialysis procedure with a patient. The instructions are also for causing the one or more processing devices to, if at least one of the first USB data line or the second USB data line goes to a high state, monitor an output of a current detection circuit. The output is indicative of whether power is or is not being drawn from the dialysis device by a USB peripheral device connected to the dialysis device.

Implementations may include one or more of the following features.

In the one or more computer-readable media, the instructions may also include instructions for causing the one or more processing devices to, if the output indicates that power is not being drawn from the dialysis device by the USB peripheral device, perform at least one of the following: electrically isolating the USB peripheral device from the dialysis device and the patient; or providing an indication of a potentially unsafe condition. The potentially unsafe condition may be that the USB peripheral device may be drawing power from a power supply independent of the dialysis device and thus may present a potential risk to the patient.

In the one or more computer-readable media, the dialysis device may include a USB host device capable of providing power to the USB peripheral device. The USB peripheral device may include a USB connector. The USB host device may include a USB port to receive the USB connector so that the USB peripheral device can be connected to the dialysis device.

In the one or more computer-readable media, the dialysis procedure may include hemodialysis and the dialysis device may include a hemodialysis device.

In some aspects, a method includes determining whether a serial bus peripheral device is connected to a medical device at a serial port on the medical device. The medical device is configured for use in a medical procedure with a patient. The method also includes, if the serial bus peripheral device is determined to be connected to the medical device, determining whether the serial bus peripheral device is drawing power from the medical device.

Implementations may include one or more of the following features.

In the method, the serial bus peripheral device may be a USB peripheral device and the serial port may be a USB port. The serial bus peripheral device may be an IEEE (Institute of Electrical and Electronics Engineers, Inc.) 1394 High Performance Serial Bus peripheral device and the serial port may be an IEEE 1394 port. For example, the serial bus peripheral device may be a FireWire® peripheral device and the serial port may be a FireWire® port.

In the method, the medical procedure may include hemodialysis and the medical device may include a hemodialysis device.

In general, in some aspects, a method includes determining that a serial bus peripheral device is not drawing power from a medical device. The serial bus peripheral device is connected to the medical device at a serial port on the medical device. The medical device is configured for use in a medical procedure with a patient. The method also includes, responsively to the determining, providing an indication of a potentially unsafe condition to at least one of a user of the medical device or the patient. The potentially unsafe condition is that the serial bus peripheral device may be drawing power from a power supply independent of the medical device and thus may present a potential risk to the patient.

Implementations may include one or more of the following features.

In the method, the serial bus peripheral device may be a USB peripheral device and the serial port may be a USB port. The serial bus peripheral device may be an IEEE (Institute of Electrical and Electronics Engineers, Inc.) 1394 High Performance Serial Bus peripheral device and the serial port may be an IEEE 1394 port. For example, the serial bus peripheral device may be a FireWire® peripheral device and the serial port may be a FireWire® port.

In the method, the medical procedure may include hemodialysis and the medical device may include a hemodialysis device.

The foregoing methods may be implemented as one or more computer-readable media storing instructions that are executable on one or more processing devices to implement the methods. The one or more computer-readable media may be, or may include, tangible media. The foregoing methods may be implemented by one or more processing devices on one or more computing devices. The foregoing methods may be implemented as a computer program product comprised of instructions that are stored on one or more computer-readable media, and that are executable on one or more processing devices. The foregoing methods may be implemented as an apparatus or system that includes one or more processing devices and memory to store executable instructions to implement the methods.

The details of one or more examples are set forth in the accompanying drawings and the description below. Further features, aspects, and advantages will become apparent from the description, the drawings, and the claims.

DETAILED DESCRIPTION

Figure 1A:
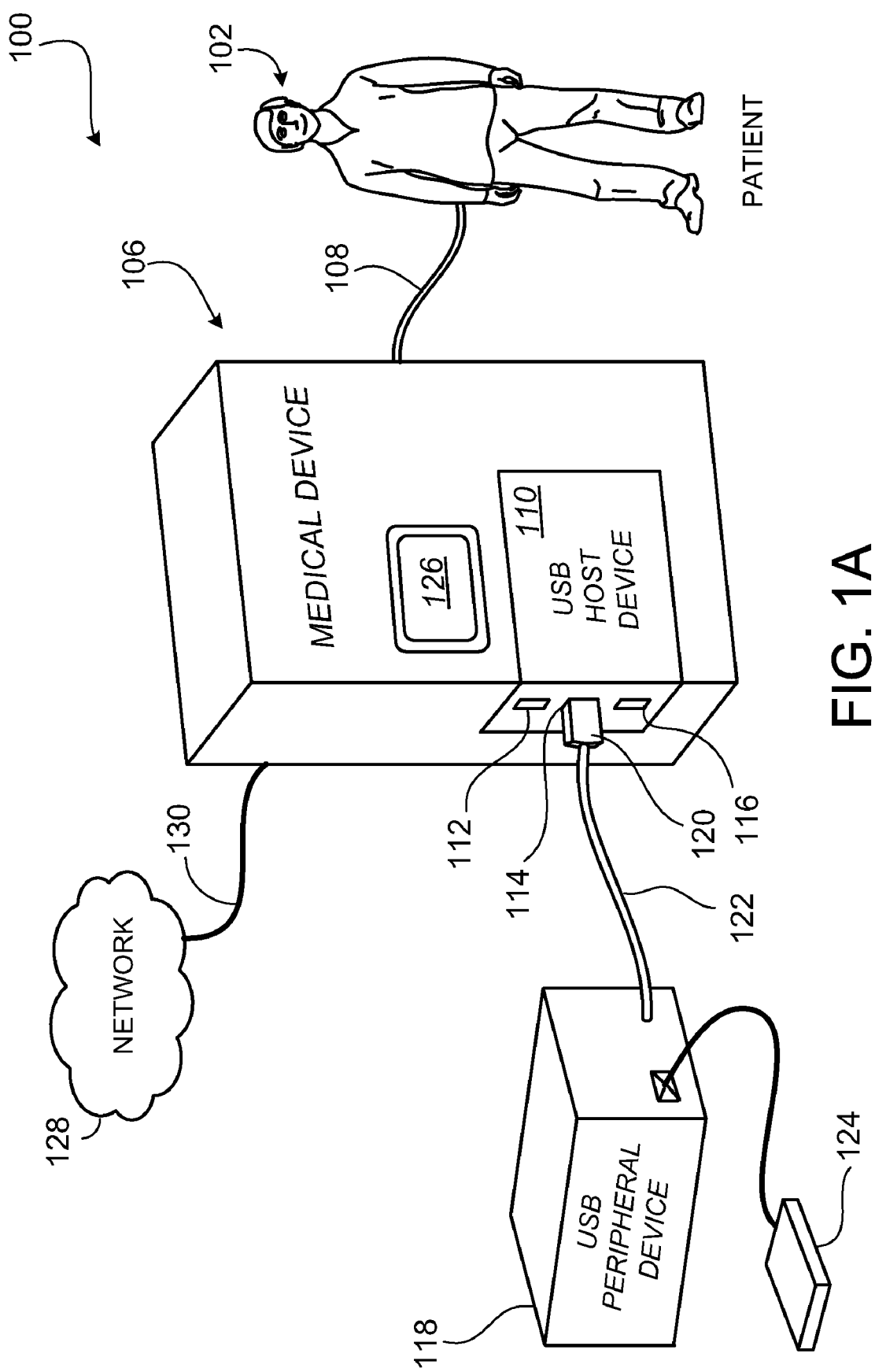
FIG. 1A is a diagram showing an example of a patient care environment that includes an example medical device.

Devices that receive power from, e.g., a wall outlet, generally must include protection from voltage surges and from leakage current. A device may include an isolation transformer to, e.g., provide voltage isolation so that the device is isolated from, e.g., a surge on an electrical outlet. Likewise, a device with an isolation transformer may be designed to limit the potential for leakage current from the power supply and through the isolation transformer to the device. That is, to protect users of the device from becoming a path to ground in the event of an electrical fault, the potential leakage current of a device may be limited.

Medical grade power supplies generally require a higher degree of protection from voltage surges and from leakage current than non-medical grade power supplies and thus must meet very strict standards. For example, a non-medical grade power supply (e.g., a power supply for a laptop computer) may only need to be isolated from, e.g., at least 2,000 volts, while a medical grade power supply may require voltage isolation level of, e.g., at least 4,000 volts before a breakdown.

Similarly, medical devices traditionally have been designed to have an extremely low leakage current (e.g., 5 microamperes ($\mu A$)) in order to prevent or limit safety risks to patients. Non-medical grade power supplies and medical devices using these power supplies may not be required to meet such strict standards.

Leakage current is a serious safety concern in medical devices because of risks to patients. Like in any device with electrical circuitry, electrical faults can occur in medical devices where, for example, a safety ground for the medical device is disconnected or fails, due to a malfunction or damage within the device, or due to, e.g., user error. An electrical fault in a medical device generally presents a much higher safety risk than in a non-medical device because direct contact to a patient is far more likely with a medical device, and such a patient may be grounded and may present a path to ground for the leakage current. If parts of the electrical system of the medical device are directly or indirectly in contact with, e.g., the patient's circulatory system, then the leakage current may find a path to ground through the patient's heart with potentially fatal consequences for the patient.

For example, in hemodialysis (discussed in more detail below) part of the patient's blood is transported from the patient's body to one side of a dialyzer filter on a hemodialysis device. On the other side of the dialyzer filter, a solution called dialysate contacts mechanical pumps in the hemodialysis device. If an electrical fault occurs relating to one of the mechanical pumps, then leakage current from the pump could find a path to ground by traveling through the dialysate, to the blood on the other side of the dialyzer filter, and back to the circulatory system of the (grounded) patient and possibly through the patient's heart. Even a small amount of leakage current can cause damage, or even death, to a patient.

Thus, medical devices, particularly devices with direct patient contact or that, e.g., break the patient's skin, are designed to have extremely low leakage current and must meet established strict standards.

Medical devices, however, only have as low a leakage current as the device with the highest leakage current connected to the medical device. That is, a medical device may be designed to have an extremely low leakage current, but if, e.g., signal lines (e.g., data or power lines) from another device with a higher potential leakage current are connected to the device, the medical device is now susceptible to the higher leakage current. If the higher leakage current is greater than medical grade requirements or than the requirements for the particular medical device, a potential safety hazard is presented.

With the advent of computer networking and the Internet, opportunities for obtaining, e.g., real-time information directly from medical devices have increased. Likewise, an increasing array of peripheral devices are available that may be advantageously serially connected to medical devices. Some medical (and other) devices may include serial ports to receive peripheral devices. For many devices having serial ports, optical isolation may be used to provide a high level of isolation when self-powered peripheral devices are connected to the serial ports.

A Universal Serial Bus (USB) peripheral device is generally connected to a USB host device, which may provide power to the peripheral device. For example, many USB peripheral devices (e.g., USB flash memory sticks and user interface devices such as keyboards or pointing devices) draw power solely from the USB host devices to which they are connected. Such a USB peripheral device, when connected to a USB port of a medical device (a USB host device), generally raises no safety issues regarding, e.g., leakage current because the USB peripheral device is powered by the medical device (the USB host device).

An increasing number of other USB peripheral devices, however, are powered by their own external power supplies (e.g., a wall outlet) and may draw no power from the USB host devices to which they are connected. Some examples of such "self-powered" USB peripheral devices include printers, scanners, video capture devices; monitors, external hard drives, audio speakers, barcode scanners, and so on. Still other USB peripheral devices (e.g., hybrid video recorders) may be configured to draw power from a USB host devices or from an external power device. Some types of USB peripheral devices (e.g., external hard drives, or keyboards) may be found in implementations that draw power from a USB host device, or in other, self-powered, implementations.

For certain types of medical devices, a self-powered USB peripheral device (whatever the variety) connected to a USB port of the medical device may generally present a potentially unsafe condition by, e.g., potentially increasing the leakage current risks to the medical device and to a patient coming into direct contact with the medical device.

A USB peripheral device generally has four signal lines: a power supply line VBUS, a signal ground line GND, and two data lines D+ and D−. USB peripheral devices may support data transfer at generally three speeds: high-speed, full-speed, and low-speed. When the USB peripheral device is first connected to a USB host device, the respective initial states of the two data lines D+ and D− (e.g., [D+ high, D− low] or [D+ low, D− high]) may generally indicate the operating data transfer speed of the USB peripheral device. Low speed USB peripheral devices identify themselves with a "high" state on the data line D− and a "low" state on the data line D+, while full speed and high speed USB peripheral devices identify themselves with a high state on the data line D+ and a low state on the data line D−. When no USB peripheral device is connected to a USB port, both data lines D+ and D− are at a low state.

Connecting a self-powered USB peripheral device to a medical device that meets strict power supply standards for, e.g., leakage current may compromise the safety of the device. Any of the four signal lines VBUS, GND, D+, and D− of a self-powered USB peripheral device would present a potential avenue for leakage current into medical device (a USB host device) to which the USB peripheral device was connected, thus leaving a patient who is grounded potentially vulnerable to the leakage current.

FIG. 1A shows an example of a patient care environment 100 that includes an example medical device 106. The medical device 106 is configured for use in a medical procedure with a patient 102 so that, e.g., the patient 102 may receive medical treatment from the medical device 106. A connector tube 108 connects the patient 102 to the medical device 106. The connector tube 108 may, e.g., transport blood or another fluid from the patient 102 to the medical device 106 and back again to the patient 102. In some implementations, the connector tube 108 may be considered part of the medical device 106. The medical device 106 may include a display and/or user interface 126 at which, e.g., information regarding the medical procedure and/or the patient may be displayed. The display and/or user interface 126 may include a touch screen at which data may be, e.g., entered by an operator of the medical device (e.g., a health care practitioner (HCP) such as, e.g., a doctor, a nurse, a patient care technician, or a home health aide). The medical device 106 may include other user interface devices (not shown in FIG. 1A) such as, e.g., a keyboard or pointing device. The medical device 106 may be configured to communicate with an external network 128, such as a local-area network or the Internet, via a wired or wireless connection 130.

The medical device 106 may include one or more processing devices. The one or more processing devices may be used to manage and oversee the functions of the medical procedure and to, for example, monitor, analyze and interpret patient vital signs and medical procedure parameters during the medical procedure.

The medical device 106 includes a Universal Serial Bus (USB) host device 110. In some implementations, the USB host device 110 may be considered to be coextensive with the medical device 106 so that, e.g., the USB host device 110 may be the medical device 106 itself. In other implementations, the medical device 106 may include, e.g., one or more devices connected to one another, with one of the devices including the USB host device 110.

In general, in some implementations, the USB host device 110 (and thus the medical device 106) may include one or more USB ports configured to receive USB connectors from USB peripheral devices. The USB host device 110 of the medical device 106 may include three USB ports 112, 114, 116 being shown in FIG. 1A. In an implementation, the connection 130 to the external network 128 may be wired and be plugged into one of the USB ports 112, 114, 116 (USB port 114 is being used in FIG. 1A).

As discussed above, while some USB peripheral devices (e.g., USB flash memory sticks) draw power solely from the USB host devices to which they are connected, other USB peripheral devices may be powered by their own external power supplies and may draw no power from the USB host devices to which they are connected.

In FIG. 1A, an example USB peripheral device 118 is connected to the medical device 116 via a cord 122 and a USB connector 120. The USB connector 120 is plugged into the USB port 114 on the USB host device 110 of the medical device 106. The USB peripheral device 118 is powered by its own external power supply 124 and draws no power from the USB host device 110 of the medical device 106. In some implementations, the cord 112, the USB connector 120, and the external power supply 124 may be considered part of the USB peripheral device 118. The USB connector 120 of FIG. 1A is a series A plug. In other implementations, series A connectors (plugs and/or receptacles) and/or series B connectors (plugs and/or receptacles) may be used.

As described above, some examples of "self-powered" USB peripheral devices include printers, scanners, video capture devices; monitors, external hard drives, audio speakers, barcode scanners, and so on.

The medical device 106 may be configured for use in a medical procedure with a patient. The medical procedure may be any of a variety of medical procedures, including, for example, an extracorporeal medical procedure in which a portion of blood is removed from the patient, the portion of the blood is processed by the medical device, and at least some of the portion of blood is subsequently returned to the patient. Even though an extracorporeal medical procedure is carried on outside of the patient's body, if the extracorporeal medical procedure is a circulatory procedure, the patient (via the circulatory system of the patient) may generally effectively be in direct contact with the medical device. The medical procedure may be, e.g., hemodialysis, and the medical device 106 may be (or may include) e.g., a hemodialysis device. An example implementation of the medical device 106 as an example hemodialysis device is described below with respect to FIG. 1B. The medical procedure may be, e.g., peritoneal dialysis, and the medical device 106 may be (or may include), e.g., a peritoneal dialysis device. In addition to or instead of hemodialysis and/or peritoneal dialysis, the medical procedure may be, e.g., hemofiltration, hemodiafiltration, plasmapheresis, apheresis, extracorporeal membrane oxygenation (ECMO), or cardiopulmonary bypass, or any combination of these. The medical procedure may include assisted blood circulation during open heart surgery and the medical device may include, e.g., a heart-lung machine. In some implementations, the medical procedure may include infusing medication into a patient's body and the medical device 106 may be (or may include), e.g., an infusion pump. In some implementations, the medical procedure may include entering a patient's body and the medical device 106 (e.g., used to enter the patient's body) may be (or may include), e.g., a surgical instrument, such as a vibrating or oscillating surgical cutting device. In some implementations in which the medical device 106 includes a surgical instrument, the connector tube 108 of FIG. 1A, may generally not be included or involved as part of the procedure. Generally, a medical procedure may involve direct contact of the medical device 106 with a bodily fluid (e.g., blood) of a patient, direct contact of an output of the medical device 106 with the patient, direct contact of the medical device with the patient's body, puncturing of the patient's skin, or any combination of these. Other examples of medical devices and equipment may include, e.g., patient monitors, external pacemakers, neurostimulators, x-ray machines, heart pumps, heart monitors, computed axial tomography (CAT or CT) equipment, magnetic resonance imaging (MRI) equipment; radiation therapy equipment, and incontinence monitors.

Figure 1B:
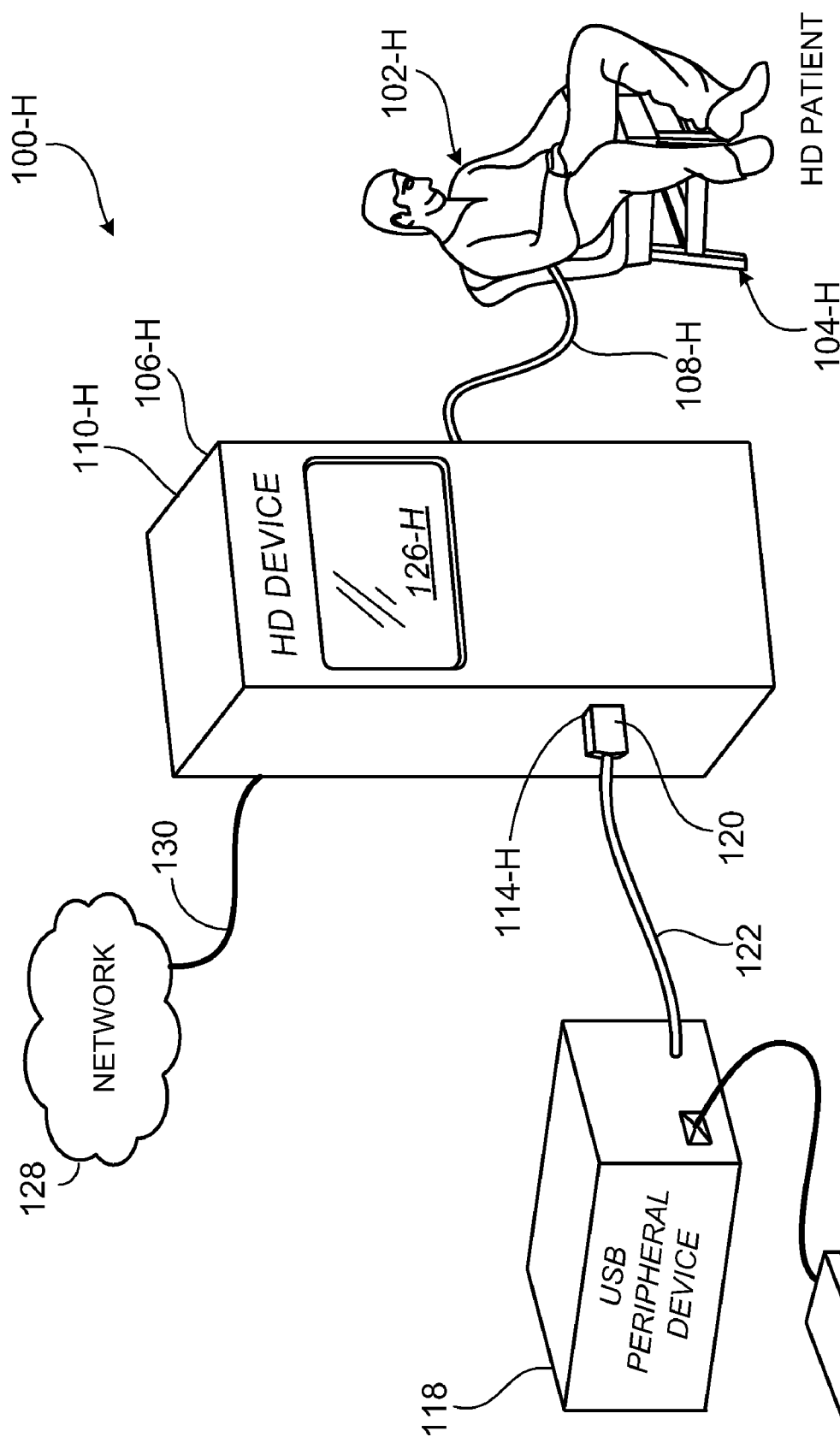
FIG. 1B is a diagram showing an example of a patient care environment that includes an example hemodialysis device.

An example of a particular type of medical device (a hemodialysis device) and particular type of medical procedure (hemodialysis) is shown in FIG. 1B. Hemodialysis is a process which employs a machine that includes a dialyzer to aid patients whose renal function has deteriorated to the point where their body cannot adequately rid itself of toxins. The dialyzer includes a semi-permeable membrane, the membrane serving to divide the dialyzer into two chambers. Blood is pumped through one chamber and a dialysis solution through the second. As the blood flows by the dialysis fluid, impurities, such as urea and creatinine, diffuse through the semi-permeable membrane into the dialysis solution. The electrolyte concentration of the dialysis fluid is set so as to maintain electrolytic balance within the patient.

Further purification in a dialyzer is possible through ultra-filtration. Ultrafiltration results from the normal situation wherein there is a positive pressure differential between the blood and the dialysis fluid chambers. This pressure differential causes water in the blood to pass through the membrane into the dialysis solution. This provides the benefit of reducing a dialysis patient's excess water load which normally would be eliminated through proper kidney functioning.

Patients undergoing dialysis therapy typically travel three or more times per week to hospital or dialysis centers that are designed for efficient and routine dialysis therapy. Hemodialysis is a complex treatment process in which, typically, an arterio-venous shunt, frequently termed a "fistula," is surgically inserted between a patient's artery and vein to facilitate transfer of blood from the patient to the dialyzer. During a normal dialysis treatment, one end of an arterial line or tube is inserted into the upstream end of the fistula (i.e., at a point near the patient's artery) and transports blood withdrawn from the upstream portion of the fistula to the inlet of the dialyzer; a venous line or tube connected to the output of the blood side of the dialyzer returns treated blood to the fistula at an insertion point downstream of the arterial line (i.e., at a point near the patient's vein).

Since dialysis involves removing blood from and returning blood to a patient, performing a dialysis procedure carries a degree of risk. Successful dialysis treatment requires monitoring of several patient vital signs and hemodialysis parameters during the dialysis process in order to optimize the overall efficacy of the dialysis procedure, to assess the condition of the fistula (the access to the patient's blood) and to determine the actual purification achieved. Some examples of parameters monitored and analyzed by a hemodialysis machine or equipment include the blood access flow rate or the rate at which blood flows out of the patient to the dialyzer, a critical parameter; and the ratio Kt/V to measure dialysis efficiency, where K is the clearance or dialysance (both terms representing the purification efficiency of the dialyzer), t is treatment time and V is the patient's total water value.

FIG. 1B shows an example of a patient care environment 100-H that includes a example hemodialysis (HD) device 106-H. The HD device 106-H is an example implementation of the medical device 106. The HD device 106-H is configured for use in hemodialysis with a hemodialysis (HD) patient 102-H seated in a chair 104-H so that, e.g., the HD patient 102-H may receive hemodialysis treatment from the HD device 106-H. A connector tube or arterial line 108-H transports blood from the HD patient 102-H to the HD device 106-H and back again to the HD patient 102-H after processing and treatment in the HD device 106-H. The HD device 106-H may include a display and/or user interface 126-H at which, e.g., information regarding the hemodialysis medical procedure and/or the patient may be displayed. The display and/or user interface 126-H may include a touch screen at which data may be, e.g., entered by an operator of the HD device 106-H. The HD device 106-H may include other user interface devices (not shown in FIG. 1B) such as, e.g., a keyboard or pointing device. As in FIG. 1A, the HD device 106-H may be configured to communicate with the external network 128 via the wired or wireless connection 130.

The HD device 106-H may include one or more processing devices. The one or more processing devices may be used to manage and oversee the functions of the hemodialysis medical procedure and to, for example, monitor, analyze and interpret patient vital signs and hemodialysis parameters during the hemodialysis medical procedure.

The example HD device 106-H includes, and is coextensive with, a USB host device 110-H. In other implementations, the HD device 106-H may include, e.g., one or more devices connected to one another, with one of the devices including the USB host device 110-H.

The HD device 106-H (or USB host device 110-H) may include one or more USB ports, with one USB port 114-H being shown in FIG. 1B. The example USB peripheral device 118 is connected to the HD device 106-H via the cord 122 and the USB connector 120. The USB connector 120 is plugged into the USB port 114-H on the USB host device 110-H (or HD device 106-H). The USB peripheral device 118 is powered by its own external power supply 124 and draws no power from the USB host device 110-H of the HD device 106-H.

Figure 2:
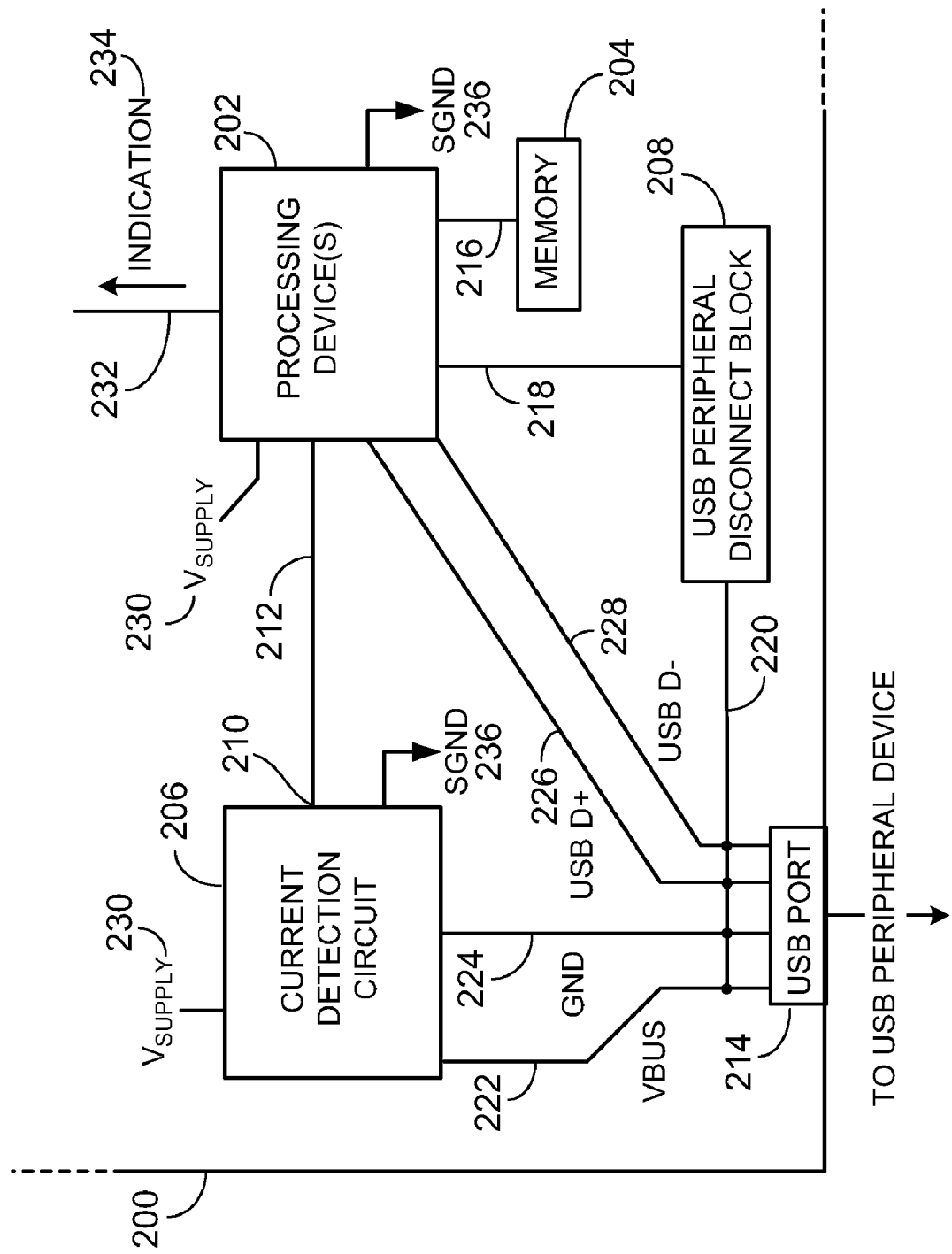
FIG. 2 is a block diagram of a portion of an example medical device.

FIG. 2 is a block diagram of a portion of an example implementation 200 of the medical device 106 of FIG. 1A (or, e.g., of example implementations of the medical device 106 such as the HD device 106-H of FIG. 1B). The medical device 200 includes one or more processing devices 202, memory 204, a current detection circuit 206, and a USB port 214.

In some implementations, the medical device 200 may include a USB peripheral disconnect block 208. In other implementations, the medical device 200 does not include the block 208. Although only one USB port 214 is shown in FIG. 2, in some implementations, the medical device 200 may include other USB ports. Each other USB port may have its own corresponding respective separate current detection circuit and its own respective separate USB peripheral disconnect block. The USB ports may also be used in, e.g., a time sharing arrangement with one or more current detection circuit and one or more USB peripheral disconnect blocks.

The current detection circuit 206 and, e.g., the one or more processing devices 202 each receive a power supply voltage $V_{SUPPLY}$ 230 for the medical device 200, and are both connected to a signal ground SGND 236 for the medical device 200. The current detection circuit 206 is connected at an output 210 of the current detection circuit 206 to a connection 212 that goes to the one or more processing devices 202. Memory 204 and the USB peripheral disconnect block 208 are connected to the one or more processing devices 202 via respective connections 216, 218.

The USB port 214 interfaces with four signal lines 222, 224, 226, 228. VBUS 222 is the power supply line for a USB peripheral device (e.g., USB peripheral device 118) connected to the USB port 214. GND 224 is the signal ground line for the USB peripheral device. Two USB data lines, USB D+ 226 and USB D− 228, are the data lines for the USB peripheral device.

The current detection circuit 206 is connected to the USB port 214 via the signal lines VBUS 222 and GND 224. The one or more processing devices 202 receive the pair of USB data lines, USB D+ 226 and USB D− 228. The USB peripheral disconnect block 208 may provide isolation (e.g., electrical isolation) of the medical device 200 from the USB port 214 and any USB peripheral device connected to the USB port 214. For example, the USB peripheral disconnect block 208 may be configured to disconnect (e.g., switch off) one or more of the signal lines 222, 224, 226, 228 at connection 220. To fully electrically isolate and more adequately protect the medical device 200 (and any patient receiving medical treatment from the medical device 200), the USB peripheral disconnect block 208 may generally configured to disconnect (e.g., switch off) all four of the signal lines at once so that the medical device 200 is not susceptible to leakage current from the attached USB peripheral device.

The medical device 200 may be configured to determine whether a USB peripheral device, such as the USB peripheral device 118, is attached to the medical device 200.

For example, in some implementations, the one or more processing devices 202 may monitor the pair of USB data lines, USB D+ 226 and USB D− 228. As described above, when a USB peripheral device, such as USB peripheral device 118, is first connected to a USB port such as, e.g., USB port 214, at least one of the USB data lines will go to a high state. The one of more processing devices 202 may be configured to sense transitions of the USB data lines 226, 228 just after or shortly after a USB peripheral device 118 is plugged into a USB port so that if at least one of the first USB data line USB D+ 226 or the second USB data line USB D− 228 goes to a high state, the one or more processing devices 202 may determine that the USB peripheral device 118 is connected to the medical device 200.

In some implementations, the one or more processing devices 202 may poll the first and second USB data lines 226, 228 to determine whether one or both of the first and second USB data lines 226, 228 have gone to a high state. The one or more processing devices 202 may poll the data lines 226, 228 periodically, e.g., every millisecond, or every few milliseconds.

In some implementations, an interrupt of the one or more processing devices 202 may be triggered if at least one of the first and second USB data lines 226, 228 go to a high state. At that point, the one or more processing devices may poll the first and second USB data lines 226, 228 to confirm that a USB peripheral device is connected to the medical device 200.

The medical device 200 may be configured to determine whether an attached USB peripheral device, such as the USB peripheral device 118, is drawing power from, e.g., a particular USB port of the medical device 200.

For example, in some implementations, the one or more processing devices 202 may monitor the output 210 of the current detection circuit 206. In an implementation, the current detection circuit 206 is configured to go to a "high" state (e.g., outputting a "1" at the output 210) when power is being drawn from the USB port 214 by a USB peripheral device connected to the USB port 214. In an implementation, the current detection circuit 206 is configured to go to a "low" state (e.g., outputting a "0" at the output 210) when no power (or appreciably no power) is being drawn from the USB port 214, so that, e.g., a self-powered USB peripheral device is connected to the USB port 214, or no USB peripheral device is connected to the USB port 214 at all.

In other implementations, the current detection circuit 206 may provide an analog voltage output signal, rather than a digital output signal to the one or more processing devices 202. The analog voltage output by the current detection circuit 206 may be proportional to the current measured by the circuit 206. In such implementations, the one or more processing devices 202 may include an analog to digital converter to convert the analog voltage output signals from the current detection circuit 206 to digital signals for further processing by the one or more processing devices 202.

In an implementation, the medical device 200 may generally determine whether a USB peripheral device is actually connected to the medical device 200 prior to determining whether power is being drawn from a particular USB port (or ports). Since the medical device 200 may, e.g., send an indication upon determining that power is not being drawn from a particular USB port (or ports), and this condition (the absence of a power draw) may be due to no USB peripheral device being connected in the first place, the medical device 200 may generally first confirm that a USB peripheral device is actually connected.

The one or more processing devices 202 may include a processing device dedicated to performing the tasks of, e.g., monitoring the USB data lines 226, 228 and the output 210 of the current detection circuit 206. The one or more processing devices 202 may include a processing device that performs other tasks in addition to, e.g., monitoring the USB data lines 226, 228 and the output 210 of the current detection circuit 210. The one or more processing devices 202 may include a microprocessor, such as a standard personal computer (PC) compatible processor, embedded within the medical device 200. In some implementations, the microprocessor may be configured to perform functions other than medical procedure related functions of the medical device 200. In some implementations, the microprocessor be, e.g., custom designed to control, operate and/or monitor some or all medical procedure functions of the medical device 200.

In some implementations, the one or more processing devices 202 are configured to provide an indication 234 to, e.g., a display and/or user interface (such as the display and/or user interface 126), or an audio speaker, or some other entity on the medical device 200, via a signal line 232.

The indication 234 may be, e.g., an indication of a potentially unsafe condition. The one or more processing devices 202 may be configured to provide the indication 234 if a USB peripheral device (e.g., determined by the one or more processing devices 202 to be connected to the medical device 200) is not drawing power from the medical device 200. The potentially unsafe condition may include, e.g., that the medical device 200 is potentially susceptible to a leakage current from the USB peripheral device. The leakage current may, as described above, present a potential risk to a patient who, e.g., receives medical treatment from the medical device 200. The potentially unsafe condition may include, e.g., that the USB peripheral device may be drawing power from a power supply independent of the medical device 200 and thus presents a potential risk to the patient.

Figure 4:
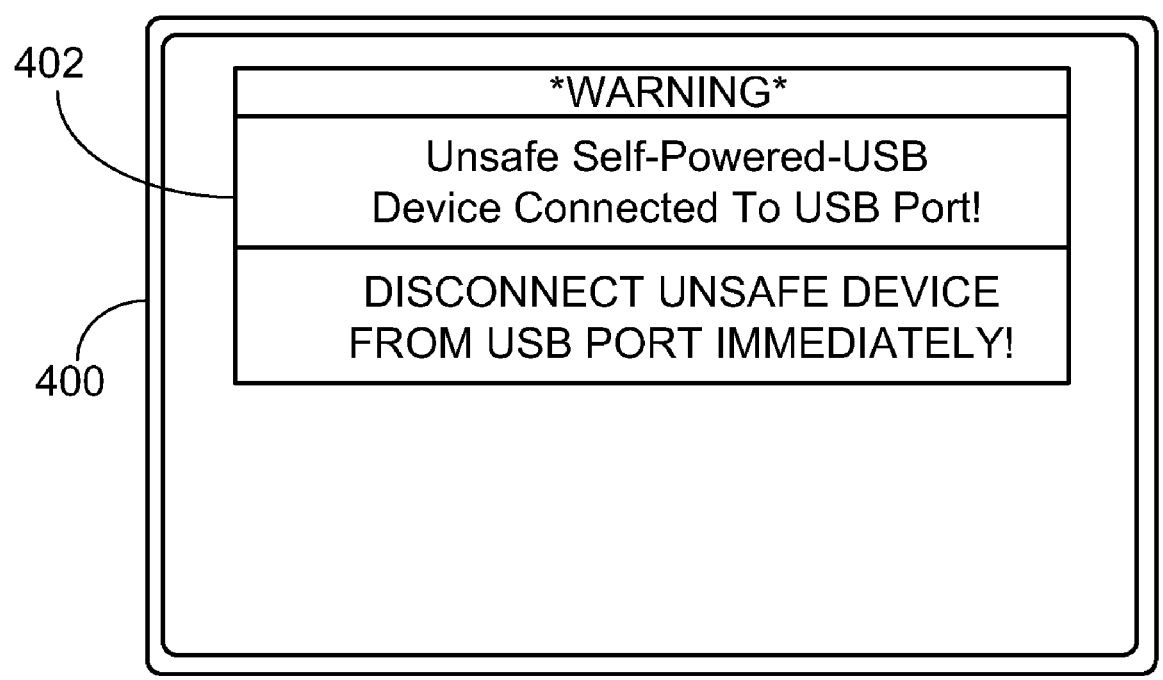
FIG. 4 is a diagram of an example medical device user interface.

The one or more processing devices 202 may provide the indication 234 by displaying a warning message on a display and/or user interface (such as the display and/or user interface 126). An example warning message is shown in FIG. 4 and is described in more detail below. The one or more processing devices 202 may provide the indication 234 by triggering an alarm. An alarm may include, e.g., an alarm sound or a synthetic voice being played through an audio speaker on the medical device 200.

Figure 3:
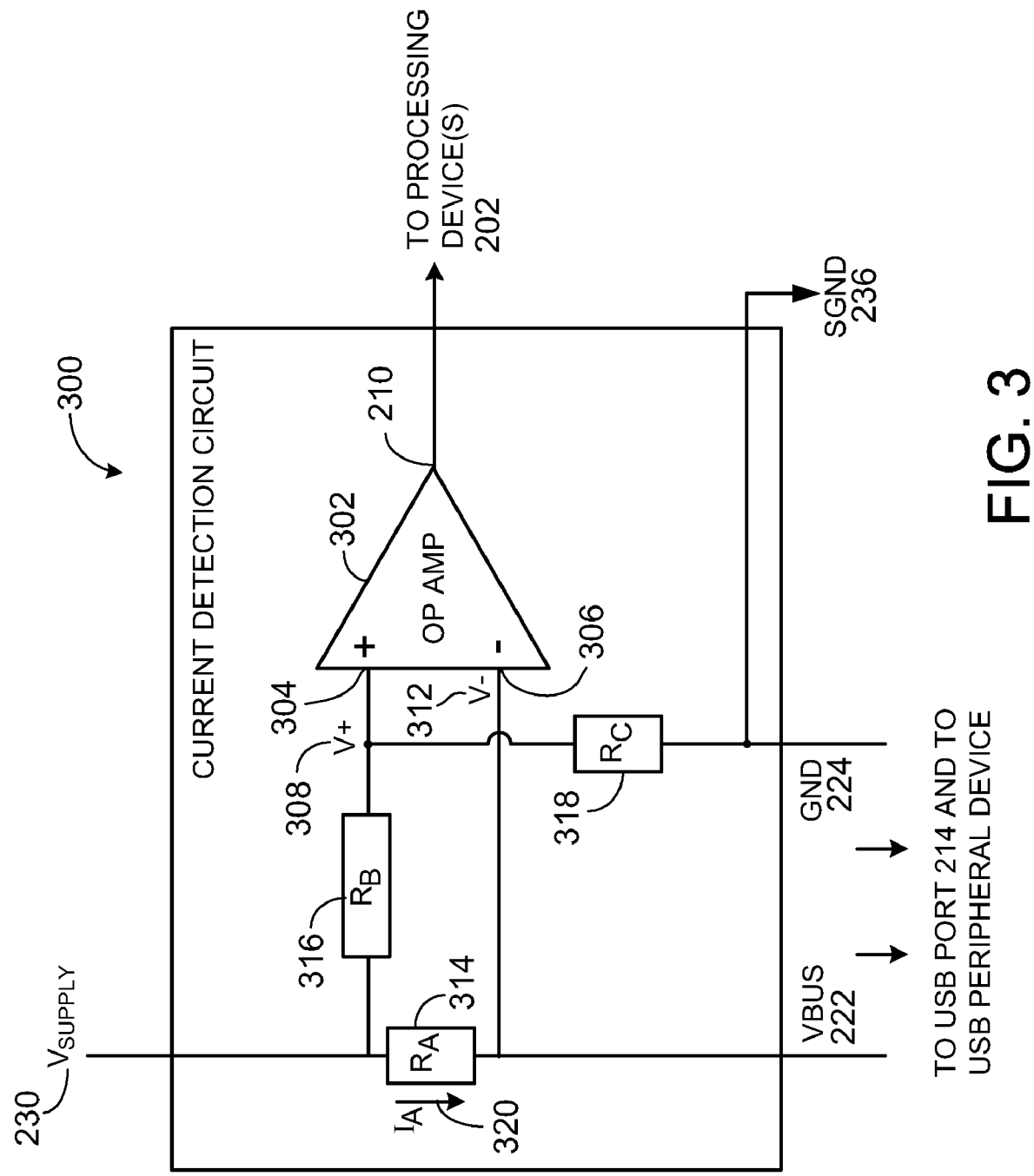
FIG. 3 is a diagram of an example current detection circuit.

FIG. 3 is a diagram of an example implementation 300 of the current detection circuit 206 of FIG. 2. The current detection circuit 300 includes an operational amplifier ("op-amp") 302 having the output 210 of FIG. 2 (connected to the one or more processing devices 202 via the connection 212), a positive input ("+") 304, and a negative input ("−") 306. The current detection circuit 300 also includes three resistors $R_A$ 314, $R_B$ 316, and $R_C$ 318.

The current detection circuit 300 receives the power supply voltage $V_{SUPPLY}$ 230 and is connected to the signal ground SGND 236 of FIG. 2. The current detection circuit 300 is connected to the USB port 214 of FIG. 2 via the signal lines VBUS 222 and GND 224. The signal ground line GND 224 may be connected to the signal ground SGND 236, e.g., within the current detection circuit 300. The resistor $R_A$ 314 is connected between the power supply voltage $V_{SUPPLY}$ 230 and the negative input 306 of the op-amp 302; the resistor $R_B$ 316 is connected between the power supply voltage $V_{SUPPLY}$ 230 and the positive input 304 of the op-amp 302; and the resistor $R_C$ 318 is connected between the signal ground SGND 326 and the positive input 304 of the op-amp 302. A current $I_A$ is shown going through the resistor $R_A$ 314.

The resistors $R_B$ 316 and $R_C$ 318 together form a voltage divider between the power supply voltage $V_{SUPPLY}$ 230 and the signal ground SGND 326 and act to set a voltage V+ 308 on the positive input 304 of the op-amp 302.

The op-amp 302 is configured to go to a "high" state (e.g., outputting a "1" at the output 210) when the voltage V+ 308 at the positive input 304 exceeds a voltage V− 312 at the negative input 306 of the op-amp 302. The op-amp 302 is configured to go to a "low" state (e.g., outputting a "0" at the output 210) when the voltage V+ 308 at the positive input 304 is less than the voltage V− 312 at the negative input 306.

In an implementation, the op-amp 302 may be configured to have a very low offset voltage (and current), so that the op-amp 302 is capable of detect a small voltage drop across the resistor $R_A$ 314 without giving a false detect (e.g., outputting a "1" at the output 210, indicating that power is being drawn by the USB peripheral device when in fact power is not being drawn). For example, the op-amp 302 may be configured to be able to measure a current as low as 5 milliamperes (mA), although this is an example value and other values and ranges may be used. In an implementation, the resistor $R_A$ 314 is designed to have a relatively low resistance when compared with the resistors $R_B$ 316 and $R_C$ 318. In an implementation, the resistor $R_B$ 316 is designed to have a relatively low resistance when compared with the resistor $R_C$ 318. For example, in an implementation, the resistor $R_A$ 314 may be 0.5 Ohms ($\Omega$), the resistors $R_B$ 316 may be 2$\Omega$, and the resistor $R_C$ 318 may be 11,000$\Omega$ (11 k$\Omega$). Of course, other resistor values may be used. The current $I_A$ drawn through the resistor $R_A$ 314 by the USB peripheral device (e.g., USB peripheral device 118) (if the device is attached to the USB port 214 and is drawing power) will often be very low because USB peripheral devices that draw power from a USB host device (e.g., USB peripheral devices such as some USB memory sticks) typically draw very little current. Moreover, a designer of the current detection circuit 300 may not want to limit the power available to an attached peripheral USB device and may try to minimize the voltage drop across the resistor $R_A$ 314.

For example, assume that the power supply voltage $V_{SUPPLY}$ 230 is 5 volts. The resistors $R_B$ 316 and $R_C$ 318 are selected to set a voltage V+ 308 of 4.97 volts on the positive input of 304 of the op-amp 302. When power is being drawn by a USB peripheral device connected to the USB port 214, the resistor $R_A$ 314 results in a voltage V− 312 of 4.96 volts on the negative input 306 of the op-amp 302. V+ 310 minus V− 312 (4.97 V−4.96 V) is positive (0.01 V), so the op-amp 302 goes to a "high" state (e.g., outputs a "1" at the output 210). When a USB peripheral device connected to the USB port 214 draws no power, there is effectively no voltage drop across the resistor $R_A$ 314, resulting in a voltage V− 312 of 5 volts. V+ 310 minus V− 312 (4.97 V−5V) is negative (−0.03 V), so the op-amp 302 goes to a "low" state (e.g., outputs a "0" at the output 210).

The current detection circuit 300 shown in FIG. 3 is an example implementation 300 of the current detection circuit 206 of FIG. 2, and any of a variety of current detection circuits may be used.

For example, a current monitoring device such as the INA138 High-Side Measurement Current Shunt Monitor from Texas Instruments® Corporation may be used as a current detection circuit. The INA138 would measure current and would output an analog voltage signal that is proportional to the current measure by the INA 138. As described above, in such an implementation, the one or more processing devices 202 of FIG. 2 may include an analog to digital converter to convert the analog voltage output signals from the current detection circuit to digital signals for further processing by the one or more processing devices 202.

FIG. 4 is a diagram of an example medical device user interface, e.g., an example implementation 400 of the display and/or user interface 126 of the medical device 106 of FIG. 1A. The user interface 400 shows a text box 402 (e.g., a flashing text box) that displays a warning indicative of a self-powered USB peripheral device being connected to a USB port (e.g., USB port 214 of FIG. 2) on the medical device 106. The example warning displayed in the text box is "*WARNING* Unsafe Self-Powered USB Device Connected To USB Port!—DISCONNECT UNSAFE DEVICE FROM USB PORT IMMEDIATELY!" Of course, this warning is merely an example, and any number of other warnings may be used. In some implementations, the warning may be accompanied by, e.g., an alarm sound or a synthetic voice being played through an audio speaker on the medical device 106.

Figure 5:
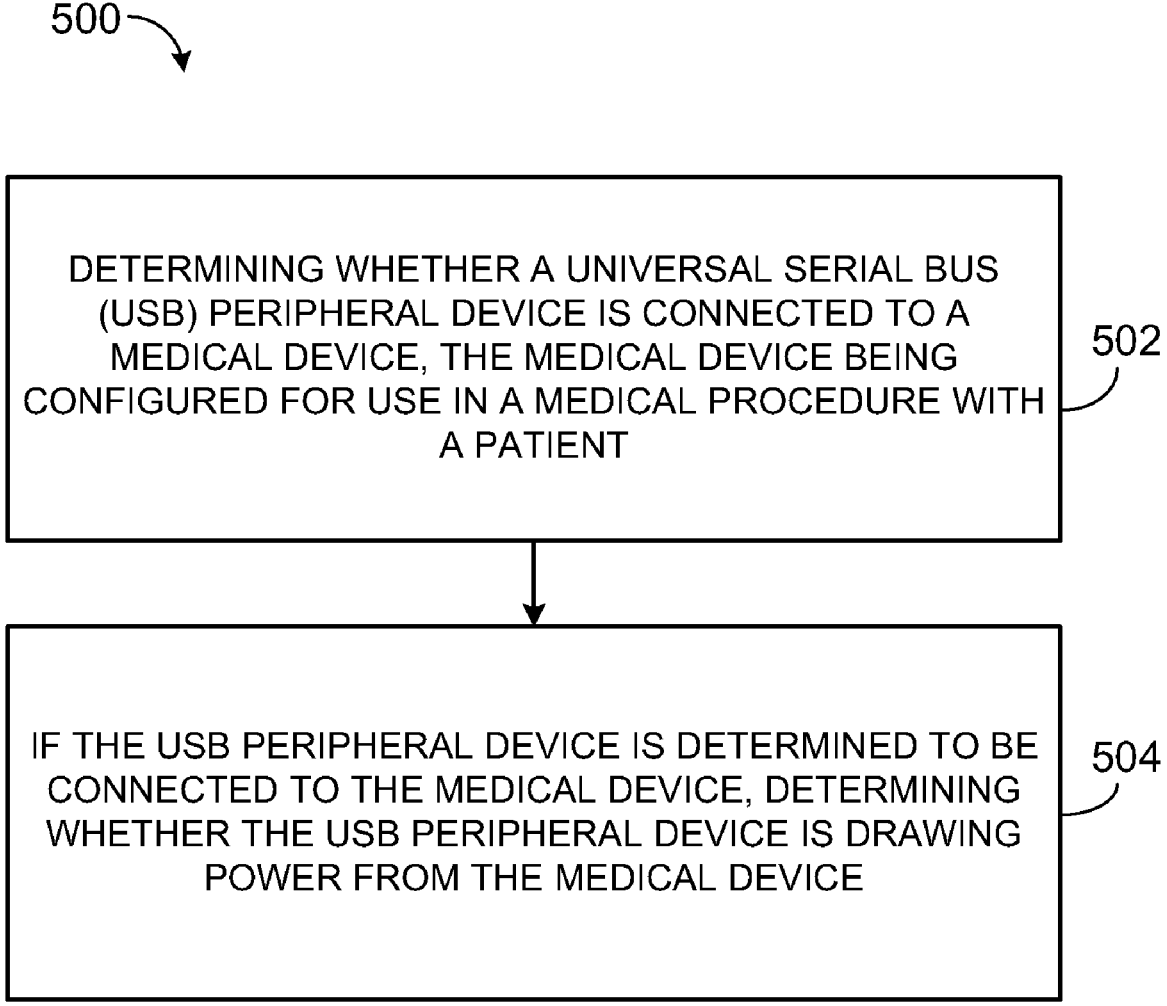
FIGS. 5-10 are flow diagrams showing example processes.

FIG. 5 is a flow diagram showing an example process 500 of one or more user interface processing devices such as, e.g., the one or more user processing devices 202 of the example medical device 200 of FIG. 2. Processing begins, for example, where the one or more user processing devices 202 determine (502) whether a USB peripheral device (e.g., USB peripheral device 118 of FIG. 1A) is connected to the medical device 200. The medical device 200 may be configured for use in a medical procedure with a patient.

If the USB peripheral device is determined to be connected to the medical device 200, the one or more user processing devices 202 determine (504) whether the USB peripheral device is drawing power from the medical device 200.

Figure 6:
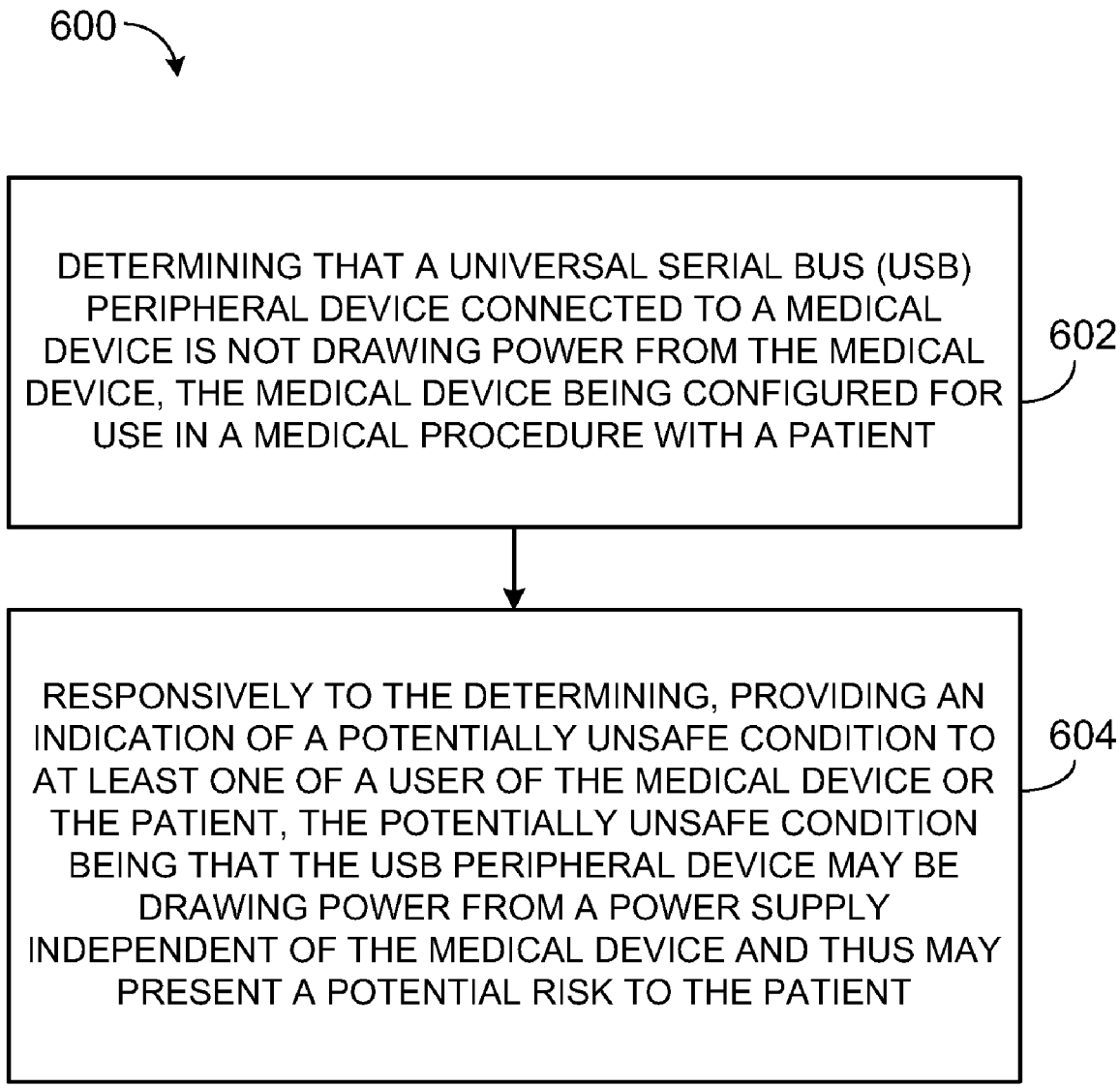

FIG. 6 is a flow diagram showing an example process 600 of one or more user interface processing devices such as, e.g., the one or more user processing devices 202 of the example medical device 200 of FIG. 2. Processing begins, for example, where the one or more user processing devices 202 determine (602) that a USB peripheral device (e.g., USB peripheral device 118 of FIG. 1A) connected to the medical device 200 is not drawing power from the medical device 200. The medical device 200 may be configured for use in a medical procedure with a patient.

Responsively to the determining, the one or more user processing devices 202 provide (604) an indication (e.g., the indication 234 of FIG. 2) of a potentially unsafe condition to at least one of a user of the medical device 200 or the patient. The potentially unsafe condition may be that the USB peripheral device may be drawing power from a power supply (e.g., external power supply 124) independent of the medical device 200 and thus may present a potential risk to the patient.

Figure 7:
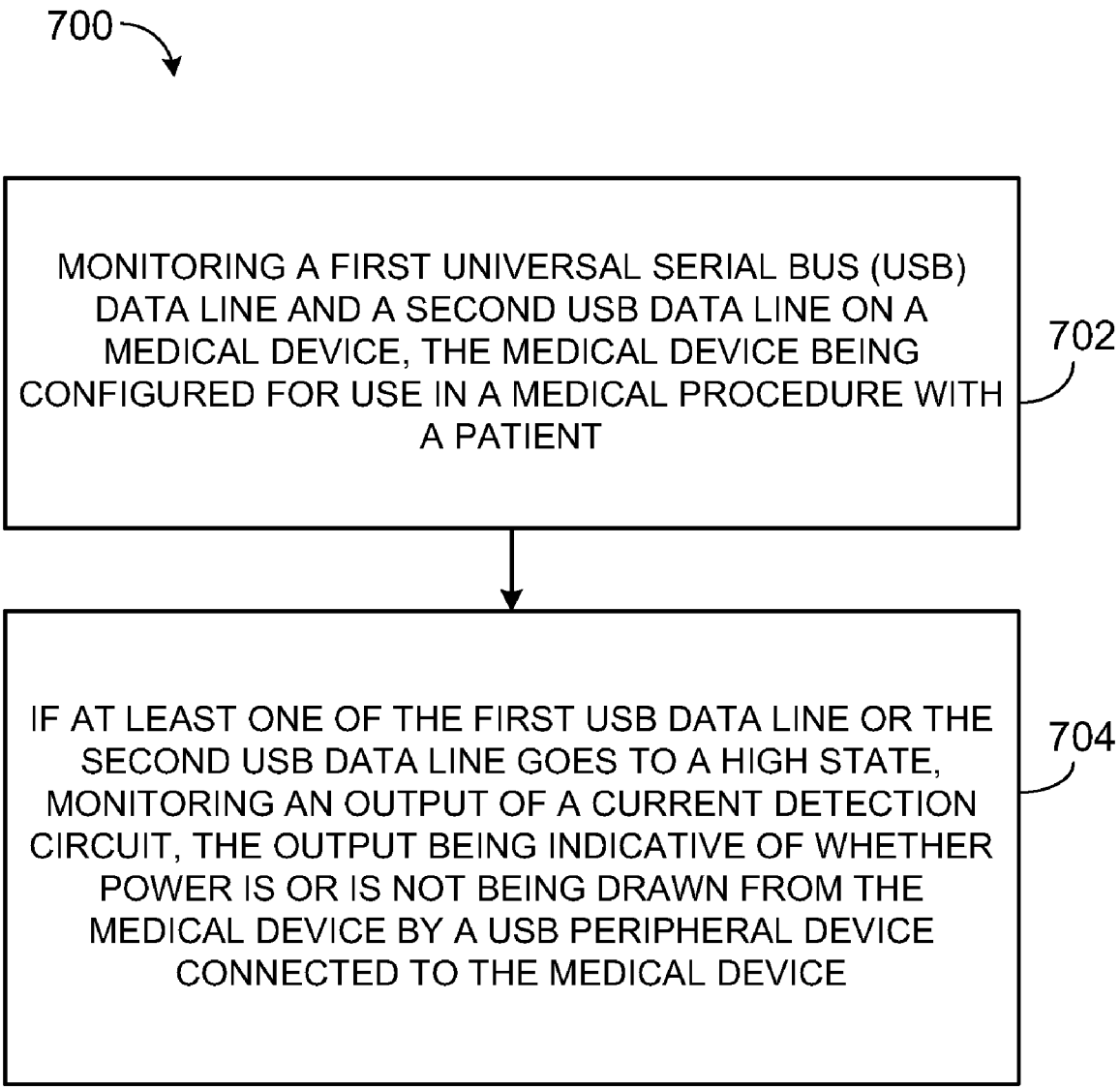

FIG. 7 is a flow diagram showing an example process 700 of one or more user interface processing devices such as, e.g., the one or more user processing devices 202 of the example medical device 200 of FIG. 2. Processing begins, for example, where the one or more user processing devices 202 monitor (702) a first USB data line (e.g., USB data line D+ 226 of FIG. 2) and a second USB data line (e.g., USB data line D− 228 of FIG. 2) on the medical device 200. The medical device 200 may be configured for use in a medical procedure with a patient.

If at least one of the first USB data line or the second USB data line goes to a "high" state, monitoring (704) an output (e.g., the output 210) of a current detection circuit (such as, e.g., the current detection circuit 206 of FIG. 2). The output may be indicative of whether power is or is not being drawn from the medical device 200 by a USB peripheral device (e.g., USB peripheral device 118 of FIG. 1A) connected to the medical device 200. When the USB peripheral device is connected to the medical device 200, the first and second USB data lines may generally be connected to respective data lines from the USB peripheral device.

Figure 8:
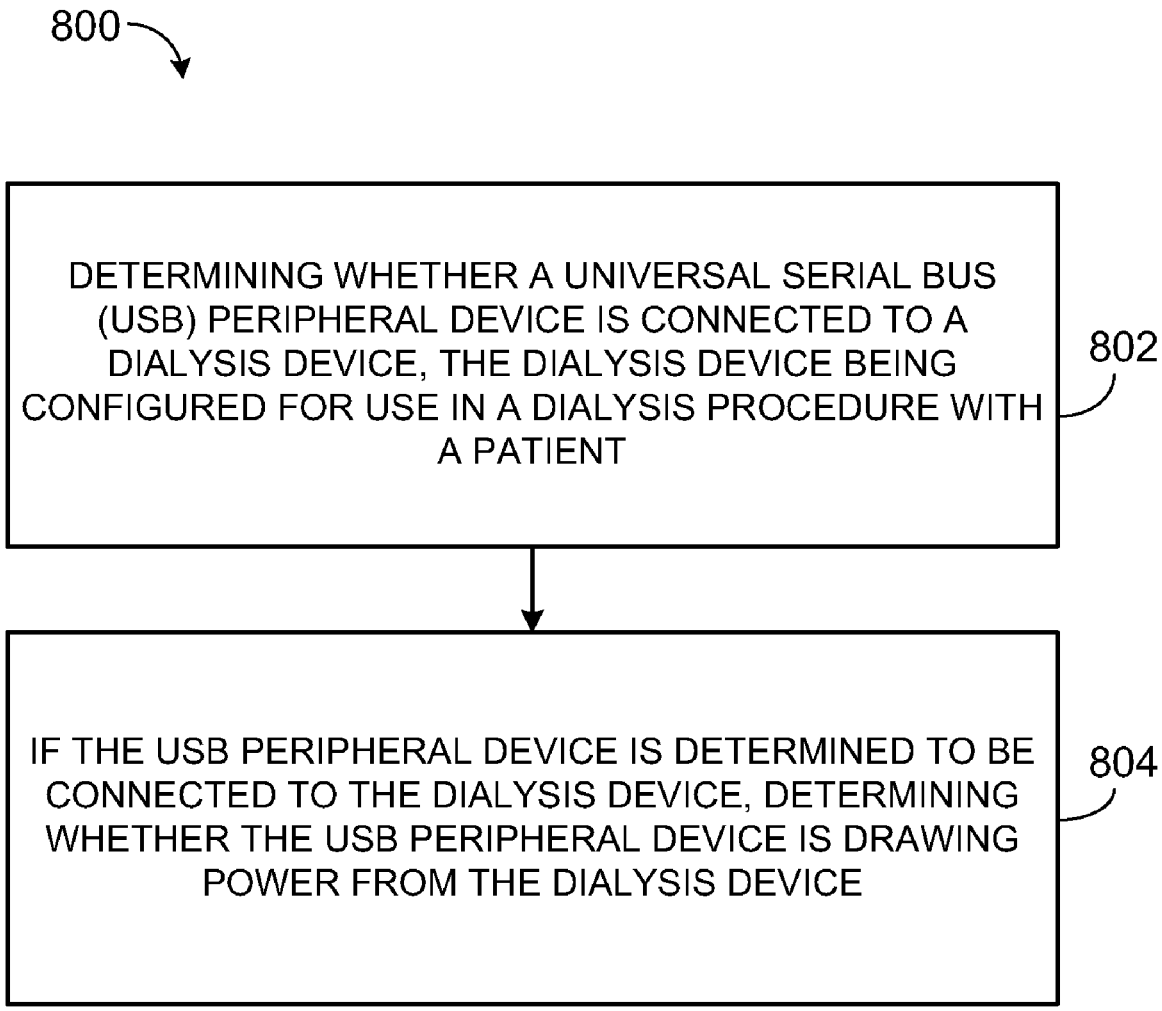

FIG. 8 is a flow diagram showing an example process 800 of one or more user interface processing devices such as, e.g., the one or more user processing devices 202 of the example medical device 200 of FIG. 2, where, here, the medical device 200 is a dialysis device, e.g., the HD device 106-H of FIG. 2. Processing begins, for example, where the one or more user processing devices 202 determine (802) whether a USB peripheral device (e.g., USB peripheral device 118 of FIG. 1B) is connected to the dialysis device. The dialysis device may be configured for use in a dialysis procedure with a patient.

If the USB peripheral device is determined to be connected to the dialysis device, the one or more user processing devices 202 determine (804) whether the USB peripheral device is drawing power from the dialysis device.

Figure 9:
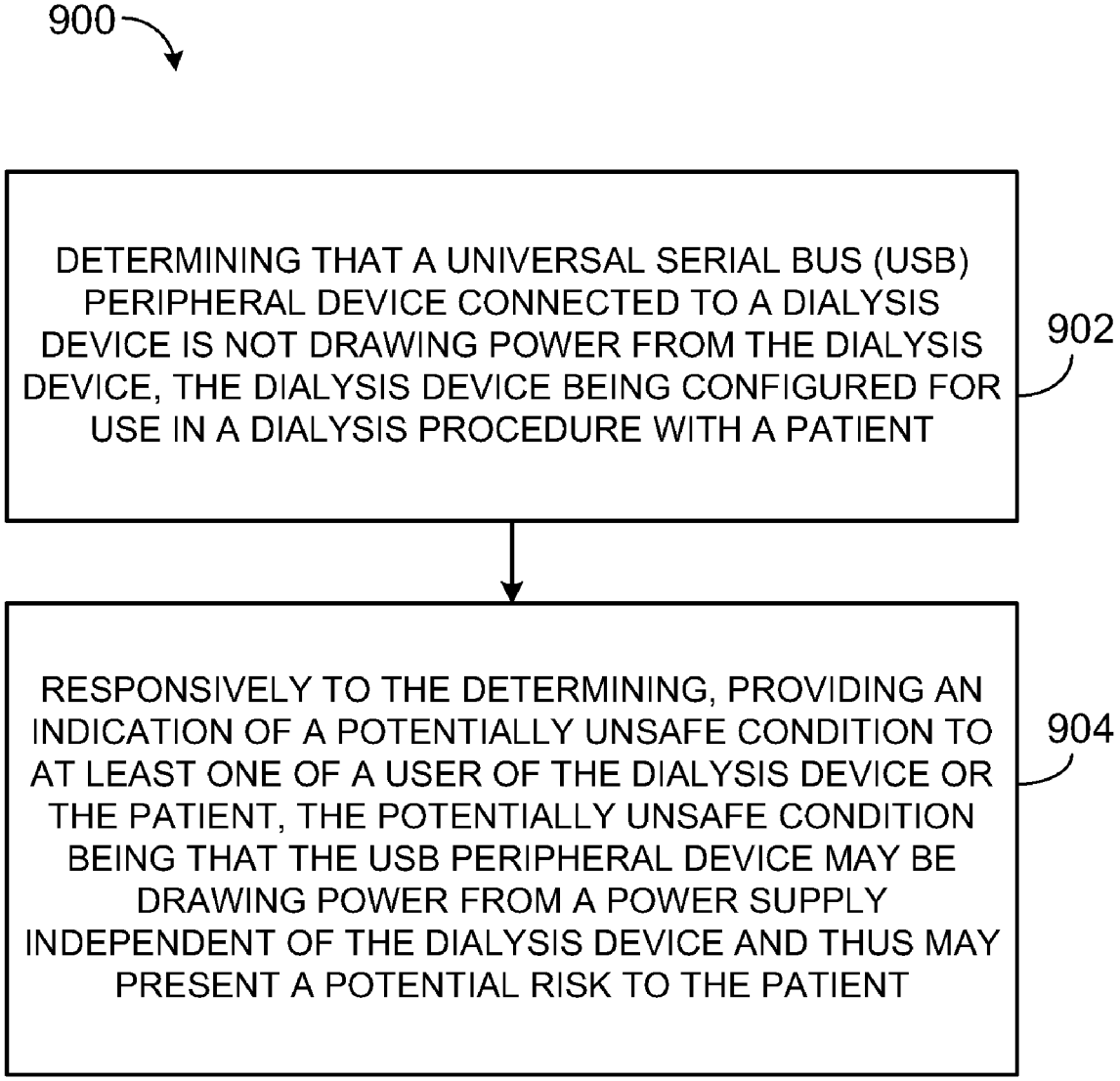

FIG. 9 is a flow diagram showing an example process 900 of one or more user interface processing devices such as, e.g., the one or more user processing devices 202 of the example medical device 200 of FIG. 2, where, here, the medical device 200 is a dialysis device, e.g., the HD device 106-H of FIG. 2. Processing begins, for example, where the one or more user processing devices 202 determine (902) that a USB peripheral device (e.g., USB peripheral device 118 of FIG. 1B) connected to the dialysis device is not drawing power from the dialysis device. The dialysis device may be configured for use in a dialysis procedure with a patient.

Responsively to the determining, the one or more user processing devices 202 provide (904) an indication (e.g., the indication 234 of FIG. 2) of a potentially unsafe condition to at least one of a user of the dialysis device or the patient. The potentially unsafe condition may be that the USB peripheral device may be drawing power from a power supply (e.g., external power supply 124) independent of the dialysis device and thus may present a potential risk to the patient.

Figure 10:
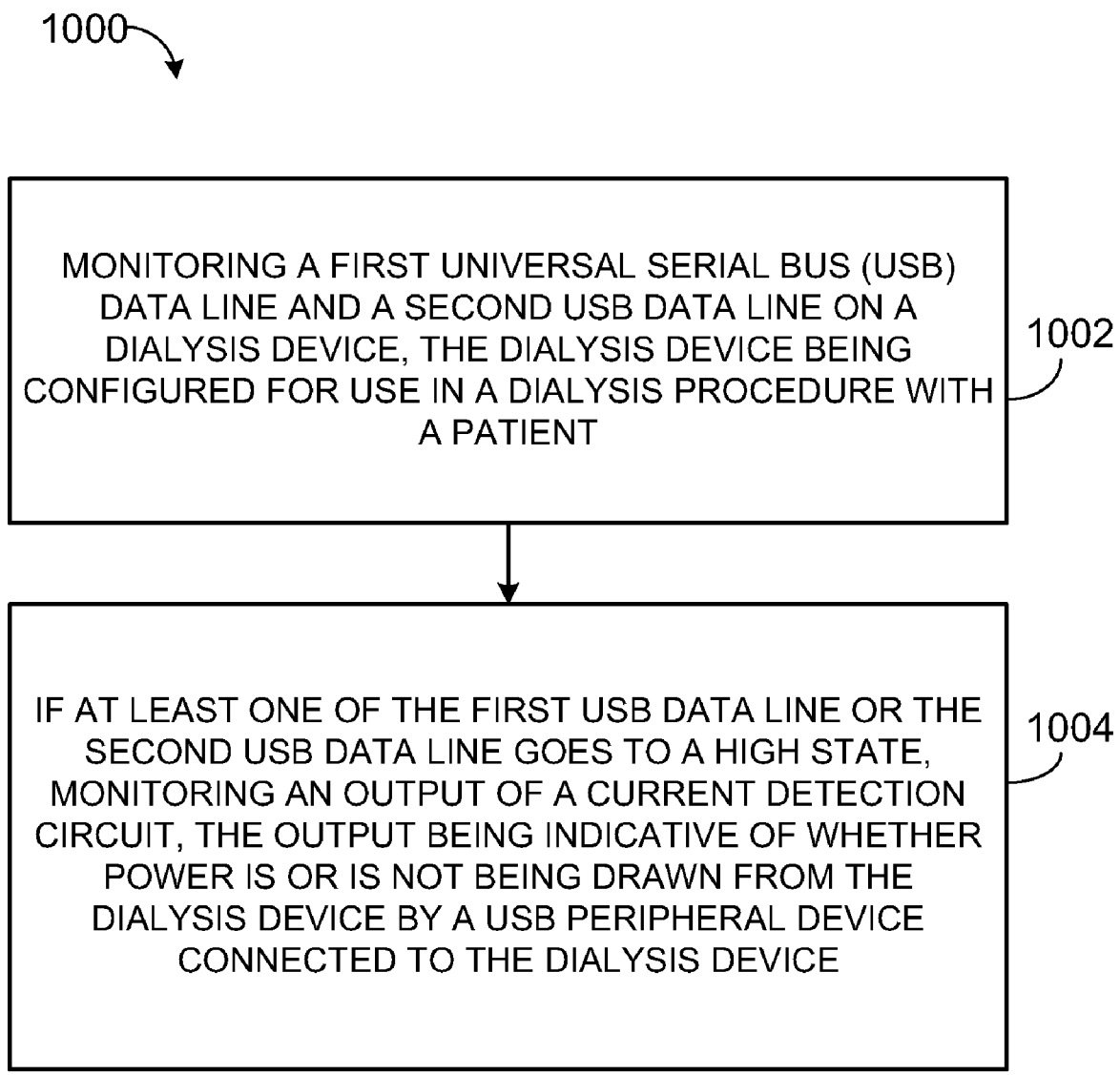

FIG. 10 is a flow diagram showing an example process 1000 of one or more user interface processing devices such as, e.g., the one or more user processing devices 202 of the example medical device 200 of FIG. 2, where, here, the medical device 200 is a dialysis device, e.g., the HD device 106-H of FIG. 2. Processing begins, for example, where the one or more user processing devices 202 monitor (1002) a first USB data line (e.g., USB data line D+ 226 of FIG. 2) and a second USB data line (e.g., USB data line D− 228 of FIG. 2) on the dialysis device. The dialysis device may be configured for use in a dialysis procedure with a patient.

If at least one of the first USB data line or the second USB data line goes to a "high" state, monitoring (1004) an output (e.g., the output 210) of a current detection circuit (such as, e.g., the current detection circuit 206 of FIG. 2). The output may be indicative of whether power is or is not being drawn from the dialysis device by a USB peripheral device (e.g., USB peripheral device 118 of FIG. 1B) connected to the dialysis device. When the USB peripheral device is connected to the dialysis device, the first and second USB data lines may generally be connected to respective data lines from the USB peripheral device.

Although the techniques described herein have been explained with reference to USB ports, USB peripheral device, etc., the techniques may be applied to other serial data port technologies, such as the IEEE (Institute of Electrical and Electronics Engineers, Inc.) 1394 High Performance Serial Bus (e.g., FireWire® of Apple® Corporation, i.LINK® of Sony® Corporation, and OHCI-Lynx® of Texas Instruments® Corporation).

Connections may be wired and/or wireless connections. When one component is said to be connected to another component, the component may be directly connected or indirectly connected (via, e.g., still another component) to the other component.

The processes described herein and their various modifications (hereinafter "the processes"), are not limited to the hardware and software described above. All or part of the processes can be implemented, at least in part, via a computer program product, e.g., a computer program tangibly embodied in an information carrier, such as one or more computer-readable media, for execution by, or to control the operation of, one or more data processing apparatus, e.g., a programmable processor, a computer, multiple computers, and/or programmable logic components.

A computer program can be written in any form of programming language, including compiled or interpreted languages, and it can be deployed in any form, including as a stand-alone program or as a module, component, subrouting, or other unit suitable for use in a computing environment. A computer program can be deployed to be executed on one computer or on multiple computers at one site or distributed across multiple sites and interconnected by a network.

Actions associated with implementing all or part of the processes can be performed by one or more programmable processing devices executing one or more computer programs to perform the functions of the processes. All or part of the processes can be implemented as, special purpose logic circuitry, e.g., an FPGA (field programmable gate array) and/or an ASIC (application-specific integrated circuit).

Processing devices suitable for the execution of a computer program include, by way of example, both general and special purpose microprocessors, and any one or more processors of any kind of digital computer. Generally, a processing device will receive instructions and data from a read-only memory or a random access memory or both. Components of a computer include one or more processing devices for executing instructions and one or more memory devices for storing instructions and data.

Components of different implementations described herein may be combined to form implementations not specifically set forth above. Other implementations not specifically described are also within the scope of the following claims.

What is claimed is:

1. A method, comprising:
    determining whether a universal serial bus (USB) peripheral device is connected to a medical device, the medical device being configured for use in a medical procedure with a patient;
    if the USB peripheral device is determined to be connected to the medical device, determining whether the USB peripheral device is drawing power from the medical device; and
    if the USB peripheral device is determined to not be drawing power from the medical device, providing an indication of a potentially unsafe condition, the potentially unsafe condition being that the USB peripheral device may be drawing power from a power supply independent of the medical device and thus may present a potential risk to the patient.

2. The method of claim 1, wherein providing the indication comprises at least one of the following:

displaying a warning message on a user interface, the medical device comprising the user interface; or triggering an alarm.

3. The method of claim 1, further comprising:
if the USB peripheral device is determined to not be drawing power from the medical device, electrically isolating the USB peripheral device from the medical device and the patient.

4. The method of claim 3, wherein electrically isolating the USB peripheral device from the medical device and the patient comprises:
disconnecting one or more signal lines connected to a USB port of the medical device, the USB port configured to receive a USB connector of the USB peripheral device.

5. The method of claim 4, wherein the one or more signal lines comprise a first USB data line, a second USB data line, a USB power line, and a USB ground line.

6. The method of claim 1, wherein the medical device comprises a USB host device capable of providing power to the USB peripheral device, the USB peripheral device comprising a USB connector, the USB host device comprising a USB port to receive the USB connector so that the USB peripheral device can be connected to the medical device.

7. The method of claim 1, wherein the medical device comprises one or more processing devices.

8. The method of claim 7, wherein determining whether the USB peripheral device is connected to the medical device comprises:
monitoring a first USB data line and a second USB data line using the one or more processing devices; and
if at least one of the first USB data line or the second USB data line goes to a high state, determining that the USB peripheral device is connected to the medical device.

9. The method of claim 7, wherein determining whether the USB peripheral device is connected to the medical device comprises:
triggering an interrupt of the one or more processing devices if at least one of a first USB data line or a second USB data line goes to a high state.

10. The method of claim 9, wherein determining whether the USB peripheral device is connected to the medical device further comprises:
polling the first USB data line and the second USB data line using the one or more processing devices to confirm that the USB peripheral device is connected to the medical device.

11. The method of claim 7, wherein determining whether the USB peripheral device is drawing power from the medical device comprises:
monitoring an output of a current detection circuit using the one or more processing devices, the medical device comprising the current detection circuit; and
if the output is at a low state, determining that the USB peripheral device is not drawing power from the medical device.

12. The method of claim 11, wherein the current detection circuit comprises:
an operational amplifier, the operational amplifier comprising a positive input, a negative input, and the output of the current detection circuit;
a first resistor connected between a power supply of the medical device and the positive input;
a second resistor connected between a signal ground of the medical device and the positive input, the first and the second resistors forming a voltage divider between the power supply and the signal ground; and
a third resistor connected between the power supply and the negative input.

13. The method of claim 12, wherein the output is at a low state when a first voltage at the positive input is less than a second voltage at the negative input.

14. The method of claim 1, wherein the medical procedure comprises hemodialysis and the medical device comprises a hemodialysis device.

15. The method of claim 1, wherein the medical procedure comprises an extracorporeal medical procedure in which a portion of blood is removed from the patient, the portion of the blood is processed by the medical device, and at least some of the portion of blood is subsequently returned to the patient.

16. The method of claim 1, wherein the medical procedure comprises peritoneal dialysis and the medical device comprises a peritoneal dialysis device.

17. A medical device, comprising:
a memory, the memory configured to store instructions for execution; and
one or more processing devices configured to execute the instructions, the instructions for causing the one or more processing devices to:
determine whether a universal serial bus (USB) peripheral device is connected to the medical device, the medical device being configured for use in a medical procedure with a patient;
if the USB peripheral device is determined to be connected to the medical device, determine whether the USB peripheral device is drawing power from the medical device; and
if the USB peripheral device is determined to not be drawing power from the medical device, provide an indication of a potentially unsafe condition, the potentially unsafe condition being that the USB peripheral device may be drawing power from a power supply independent of the medical device and thus may present a potential risk to the patient.

18. The medical device of claim 17, wherein the instructions further comprise instructions for causing the one or more processing devices to:
if the USB peripheral device is determined to not be drawing power from the medical device, electrically isolate the USB peripheral device from the medical device and the patient.

19. The medical device of claim 17, wherein the medical device comprises a USB host device capable of providing power to the USB peripheral device, the USB peripheral device comprising a USB connector, the USB host device comprising a USB port to receive the USB connector so that the USB peripheral device can be connected to the medical device, the USB host device comprising the memory and the one or more processing devices.

20. The medical device of claim 17, wherein determining whether the USB peripheral device is connected to the medical device comprises:
monitoring a first USB data line and a second USB data line; and
if at least one of the first USB data line or the second USB data line goes to a high state, determining that the USB peripheral device is connected to the medical device.

21. The medical device of claim 17, further comprising:
a current detection circuit; and
wherein determining whether the USB peripheral device is drawing power from the medical device comprises:
monitoring an output of the current detection circuit; and if the output is at a low state, determining that the USB peripheral device is not drawing power from the medical device.

22. The medical device of claim 21, wherein the current detection circuit comprises:
an operational amplifier, the operational amplifier comprising a positive input, a negative input, and the output of the current detection circuit;
a first resistor connected between a power supply of the medical device and the positive input;
a second resistor connected between a signal ground of the medical device and the positive input, the first and the second resistors forming a voltage divider between the power supply and the signal ground; and
a third resistor connected between the power supply and the negative input.

23. The medical device of claim 17, wherein the medical procedure comprises hemodialysis and the medical device comprises a hemodialysis device.

24. One or more computer-readable media storing executable instructions, the one or more computer-readable media comprising tangible media, the instructions for causing one or more processing devices to:
determine whether a universal serial bus (USB) peripheral device is connected to a medical device, the medical device comprising the one or more processing devices, the medical device being configured for use in a medical procedure with a patient;
if the USB peripheral device is determined to be connected to the medical device, determine whether the USB peripheral device is drawing power from the medical device; and
if the USB peripheral device is determined to not be drawing power from the medical device, provide an indication of a potentially unsafe condition, the potentially unsafe condition being that the USB peripheral device may be drawing power from a power supply independent of the medical device and thus may present a potential risk to the patient.

25. The one or more computer-readable media of claim 24, wherein the instructions further comprise instructions for causing the one or more processing devices to:
if the USB peripheral device is determined to not be drawing power from the medical device, electrically isolate the USB peripheral device from the medical device and the patient.

26. The one or more computer-readable media of claim 24, wherein the medical device comprises a USB host device capable of providing power to the USB peripheral device, the USB peripheral device comprising a USB connector, the USB host device comprising a USB port to receive the USB connector so that the USB peripheral device can be connected to the medical device.

27. The one or more computer-readable media of claim 24, wherein determining whether the USB peripheral device is connected to the medical device comprises:
monitoring a first USB data line and a second USB data line; and
if at least one of the first USB data line or the second USB data line goes to a high state, determining that the USB peripheral device is connected to the medical device.

28. The one or more computer-readable media of claim 24, wherein determining whether the USB peripheral device is drawing power from the medical device comprises:
monitoring an output of a current detection circuit, the medical device comprising the current detection circuit; and if the output is at a low state, determining that the USB peripheral device is not drawing power from the medical device.

29. The one or more computer-readable media of claim 28, wherein the current detection circuit comprises:
an operational amplifier, the operational amplifier comprising a positive input, a negative input, and the output of the current detection circuit;
a first resistor connected between a power supply of the medical device and the positive input;
a second resistor connected between a signal ground of the medical device and the positive input, the first and the second resistors forming a voltage divider between the power supply and the signal ground; and
a third resistor connected between the power supply and the negative input.

30. The one or more computer-readable media of claim 24, wherein the medical procedure comprises hemodialysis and the medical device comprises a hemodialysis device.

31. A method, comprising:
determining that a universal serial bus (USB) peripheral device connected to a medical device is not drawing power from the medical device, the medical device being configured for use in a medical procedure with a patient; and
responsively to the determining, providing an indication of a potentially unsafe condition to at least one of a user of the medical device or the patient, the potentially unsafe condition being that the USB peripheral device may be drawing power from a power supply independent of the medical device and thus may present a potential risk to the patient.

32. The method of claim 31, wherein the medical procedure comprises hemodialysis and the medical device comprises a hemodialysis device.

33. A medical device, comprising:
a memory, the memory configured to store instructions for execution; and
one or more processing devices configured to execute the instructions, the instructions for causing the one or more processing devices to:
determine that a universal serial bus (USB) peripheral device connected to the medical device is not drawing power from the medical device, the medical device being configured for use in a medical procedure with a patient; and
responsively to the determining, provide an indication of a potentially unsafe condition to at least one of a user of the medical device or the patient, the potentially unsafe condition being that the USB peripheral device may be drawing power from a power supply independent of the medical device and thus may present a potential risk to the patient.

34. The medical device of claim 33, wherein the medical procedure comprises hemodialysis and the medical device comprises a hemodialysis device.

35. A method, comprising:
monitoring a first universal serial bus (USB) data line and a second USB data line on a medical device, the medical device being configured for use in a medical procedure with a patient;
if at least one of the first USB data line or the second USB data line goes to a high state, monitoring an output of a current detection circuit, the output being indicative of whether power is or is not being drawn from the medical device by a USB peripheral device connected to the medical device; and if the output indicates that power is not being drawn from the medical device by the USB peripheral device, performing at least one of the following:
  electrically isolating the USB peripheral device from the medical device and the patient; or
  providing an indication of a potentially unsafe condition, the potentially unsafe condition being that the USB peripheral device may be drawing power from a power supply independent of the medical device and thus may present a potential risk to the patient.

36. The method of claim 35, wherein the medical device comprises one or more processing devices.

37. The method of claim 36, wherein monitoring the first USB data line and the second USB data line, and monitoring the output of the current detection comprise:
  monitoring the first USB data line and the second USB data line using the one or more processing devices; and
  monitoring the output of the current detection circuit using the one or more processing devices.

38. The method of claim 37, wherein the medical device comprises a USB host device capable of providing power to the USB peripheral device, the USB peripheral device comprising a USB connector, the USB host device comprising a USB port to receive the USB connector so that the USB peripheral device can be connected to the medical device.

39. The method of claim 35, wherein the medical procedure comprises hemodialysis and the medical device comprises a hemodialysis device.

40. A medical device, comprising:
  a current detection circuit;
  a memory, the memory configured to store instructions for execution; and
  one or more processing devices configured to execute the instructions, the instructions for causing the one or more processing devices to:
    monitor a first universal serial bus (USB) data line and a second USB data line on the medical device, the medical device being configured for use in a medical procedure with a patient;
    if at least one of the first USB data line or the second USB data line goes to a high state, monitor an output of the current detection circuit, the output being indicative of whether power is or is not being drawn from the medical device by a USB peripheral device connected to the medical device; and
    if the output indicates that power is not being drawn from the medical device by the USB peripheral device, perform at least one of the following:
      electrically isolating the USB peripheral device from the medical device and the patient; or
      providing an indication of a potentially unsafe condition, the potentially unsafe condition being that the USB peripheral device may be drawing power from a power supply independent of the medical device and thus may present a potential risk to the patient.

41. The medical device of claim 40, wherein the medical procedure comprises hemodialysis and the medical device comprises a hemodialysis device.

42. The method of claim 1, wherein the medical procedure comprises at least one of hemodialysis, peritoneal dialysis, hemofiltration, hemodiafiltration, plasmapheresis, apheresis, extracorporeal membrane oxygenation, or cardiopulmonary bypass.

43. The method of claim 1, wherein the medical procedure comprises infusing medication into the patient's body and the medical device comprises an infusion pump.

44. The method of claim 1, wherein the medical procedure comprises entering the patient's body and the medical device comprises a surgical instrument.

45. The method of claim 1, wherein the medical procedure comprises a medical procedure involving at least one of direct contact of the medical device with a bodily fluid of the patient, direct contact of an output of the medical device with the patient, direct contact of the medical device with the patient's body, or puncturing of the patient's skin.

46. The medical device of claim 17, wherein the medical procedure comprises peritoneal dialysis and the medical device comprises a peritoneal dialysis device.

47. The medical device of claim 17, wherein the medical procedure comprises at least one of hemodialysis, peritoneal dialysis, hemofiltration, hemodiafiltration, plasmapheresis, apheresis, extracorporeal membrane oxygenation, or cardiopulmonary bypass.

48. The one or more computer-readable media of claim 24, wherein the medical procedure comprises peritoneal dialysis and the medical device comprises a peritoneal dialysis device.

49. The one or more computer-readable media of claim 24, wherein the medical procedure comprises at least one of hemodialysis, peritoneal dialysis, hemofiltration, hemodiafiltration, plasmapheresis, apheresis, extracorporeal membrane oxygenation, or cardiopulmonary bypass.

50. The method of claim 31, wherein the medical procedure comprises peritoneal dialysis and the medical device comprises a peritoneal dialysis device.

51. The method of claim 31, wherein the medical procedure comprises at least one of hemodialysis, peritoneal dialysis, hemofiltration, hemodiafiltration, plasmapheresis, apheresis, extracorporeal membrane oxygenation, or cardiopulmonary bypass.

52. The medical device of claim 33, wherein the medical procedure comprises peritoneal dialysis and the medical device comprises a peritoneal dialysis device.

53. The medical device of claim 33, wherein the medical procedure comprises at least one of hemodialysis, peritoneal dialysis, hemofiltration, hemodiafiltration, plasmapheresis, apheresis, extracorporeal membrane oxygenation, or cardiopulmonary bypass.

54. The method of claim 35, wherein the medical procedure comprises peritoneal dialysis and the medical device comprises a peritoneal dialysis device.

55. The method of claim 35, wherein the medical procedure comprises at least one of hemodialysis, peritoneal dialysis, hemofiltration, hemodiafiltration, plasmapheresis, apheresis, extracorporeal membrane oxygenation, or cardiopulmonary bypass.

56. The medical device of claim 40, wherein the medical procedure comprises peritoneal dialysis and the medical device comprises a peritoneal dialysis device.

57. The medical device of claim 40, wherein the medical procedure comprises at least one of hemodialysis, peritoneal dialysis, hemofiltration, hemodiafiltration, plasmapheresis, apheresis, extracorporeal membrane oxygenation, or cardiopulmonary bypass.

* * * * *